(12) United States Patent
Elahinia et al.

(10) Patent No.: US 9,561,115 B2
(45) Date of Patent: Feb. 7, 2017

(54) EXPANDABLE INTER-VERTEBRAL CAGE AND METHOD OF INSTALLING SAME

(71) Applicant: The University of Toledo, Toledo, OH (US)

(72) Inventors: Mohammad Elahinia, Toledo, OH (US); Anand Agarwal, Ottawa Hills, OH (US); Vijay Goel, Holland, OH (US); Walter Anderson, Maumee, OH (US); Cory Chapman, Maumee, OH (US)

(73) Assignee: THE UNIVERSITY OF TOLEDO, Toledo, OH (US)

( * ) Notice: Subject to any disclaimer, the term of this patent is extended or adjusted under 35 U.S.C. 154(b) by 85 days.

(21) Appl. No.: 14/345,559

(22) PCT Filed: Sep. 20, 2012

(86) PCT No.: PCT/US2012/056297
§ 371 (c)(1),
(2) Date: Mar. 18, 2014

(87) PCT Pub. No.: WO2013/043850
PCT Pub. Date: Mar. 28, 2013

(65) Prior Publication Data
US 2014/0379086 A1    Dec. 25, 2014

Related U.S. Application Data

(60) Provisional application No. 61/536,744, filed on Sep. 20, 2011.

(51) Int. Cl.
*A61F 2/44*    (2006.01)
*A61F 2/46*    (2006.01)
(Continued)

(52) U.S. Cl.
CPC ............. *A61F 2/4465* (2013.01); *A61B 1/018* (2013.01); *A61F 2/447* (2013.01); *A61F 2/4611* (2013.01);
(Continued)

(58) Field of Classification Search
CPC .... A61F 2/4611; A61F 2/4455; A61F 2/4425; A61F 2/44
(Continued)

(56) References Cited

U.S. PATENT DOCUMENTS 5,571,109 A * 11/1996 Bertagnoli ........... A61B 17/025
606/86 A
5,836,148 A * 11/1998 Fukao ..................... F16G 13/16
248/49

(Continued)

FOREIGN PATENT DOCUMENTS

JP    2003500099 A    1/2003
JP    2008520400 A    6/2008
(Continued)

OTHER PUBLICATIONS

European Extended Search Report, Application No. EP 12834152.6, dated Apr. 1, 2015.
(Continued)

*Primary Examiner* — Eduardo C Robert
*Assistant Examiner* — Michelle C Eckman
(74) *Attorney, Agent, or Firm* — MacMillan, Sobanski & Todd, LLC

(57) ABSTRACT

An inter-vertebral cage for use in repairing a damaged inter-vertebral disc includes a plurality of cage sections and a hinge element that connects adjacent ones of the cage sections together for relative movement. The hinge elements automatically urge the cage sections to move from an extended orientation to an installed orientation.

26 Claims, 15 Drawing Sheets

(51) Int. Cl.
*A61B 1/018* (2006.01)
*A61F 2/28* (2006.01)
*A61F 2/30* (2006.01)

(52) U.S. Cl.
CPC .............. *A61F 2002/2835* (2013.01); *A61F 2002/30047* (2013.01); *A61F 2002/30092* (2013.01); *A61F 2002/30464* (2013.01); *A61F 2002/30471* (2013.01); *A61F 2002/30472* (2013.01); *A61F 2002/30542* (2013.01); *A61F 2002/30545* (2013.01); *A61F 2002/30556* (2013.01); *A61F 2002/30604* (2013.01); *A61F 2002/30607* (2013.01); *A61F 2002/30609* (2013.01); *A61F 2002/30611* (2013.01); *A61F 2002/30612* (2013.01); *A61F 2002/30616* (2013.01); *A61F 2002/30637* (2013.01); *A61F 2002/30878* (2013.01); *A61F 2002/4415* (2013.01); *A61F 2002/4475* (2013.01); *A61F 2310/00017* (2013.01); *A61F 2310/00023* (2013.01); *A61F 2310/00976* (2013.01)

(58) Field of Classification Search
USPC ................................ 623/17.11–17.16; 606/99
See application file for complete search history.

(56) References Cited

U.S. PATENT DOCUMENTS

| | | | | |
|---|---|---|---|---|
| 6,110,210 | A * | 8/2000 | Norton | A61F 2/441 |
| | | | | 623/17.11 |
| 6,387,130 | B1 * | 5/2002 | Stone | A61F 2/4455 |
| | | | | 623/17.16 |
| 6,656,178 | B1 * | 12/2003 | Sanders | A61F 2/4455 |
| | | | | 606/247 |
| 7,351,262 | B2 * | 4/2008 | Bindseil | A61F 2/4455 |
| | | | | 623/17.11 |
| 7,673,440 | B2 * | 3/2010 | Blase | H02G 11/006 |
| | | | | 59/78.1 |
| 7,749,269 | B2 * | 7/2010 | Peterman | A61F 2/447 |
| | | | | 606/90 |
| 7,887,589 | B2 | 2/2011 | Glenn et al. | |
| 7,947,078 | B2 * | 5/2011 | Siegal | A61B 17/68 |
| | | | | 248/49 |
| 8,034,110 | B2 * | 10/2011 | Garner | A61F 2/4465 |
| | | | | 623/17.11 |
| 8,246,622 | B2 * | 8/2012 | Siegal | A61B 17/320016 |
| | | | | 606/79 |
| 8,328,812 | B2 * | 12/2012 | Siegal | A61B 17/320016 |
| | | | | 606/279 |
| 8,632,591 | B2 | 1/2014 | Vila et al. | |
| 8,652,143 | B2 * | 2/2014 | McClellan, III | A61F 2/4455 |
| | | | | 606/99 |
| 8,672,977 | B2 * | 3/2014 | Siegal | A61B 17/7065 |
| | | | | 606/249 |
| 8,951,288 | B2 * | 2/2015 | McGrath | A61B 17/7094 |
| | | | | 606/246 |
| 9,095,449 | B2 * | 8/2015 | McGuckin, Jr. | A61B 17/70 |
| 9,101,475 | B2 * | 8/2015 | Wei | A61F 2/30 |
| 9,101,487 | B2 * | 8/2015 | Petersheim | A61F 2/4455 |
| 9,101,491 | B2 * | 8/2015 | Rodgers | A61F 2/447 |
| 9,259,324 | B2 | 2/2016 | McGuckin, Jr. | |
| 2004/0230100 | A1 * | 11/2004 | Shluzas | A61B 17/0218 |
| | | | | 600/208 |
| 2004/0249461 | A1 * | 12/2004 | Ferree | A61F 2/2846 |
| | | | | 623/17.11 |
| 2005/0209629 | A1 * | 9/2005 | Kerr | A61B 17/025 |
| | | | | 606/192 |
| 2006/0041258 | A1 * | 2/2006 | Galea | A61F 2/4455 |
| | | | | 16/221 |
| 2006/0142858 | A1 * | 6/2006 | Colleran | A61F 2/4465 |
| | | | | 623/17.11 |
| 2006/0189999 | A1 * | 8/2006 | Zwirkoski | A61F 2/442 |
| | | | | 606/90 |
| 2006/0206178 | A1 * | 9/2006 | Kim | A61B 17/00234 |
| | | | | 607/96 |
| 2006/0247781 | A1 * | 11/2006 | Francis | A61F 2/442 |
| | | | | 623/17.16 |
| 2007/0067035 | A1 * | 3/2007 | Falahee | A61F 2/4455 |
| | | | | 623/17.11 |
| 2007/0260314 | A1 * | 11/2007 | Biyani | A61F 2/4465 |
| | | | | 623/17.11 |
| 2008/0091269 | A1 * | 4/2008 | Zipnick | A61B 17/320016 |
| | | | | 623/17.13 |
| 2008/0125865 | A1 * | 5/2008 | Abdelgany | A61F 2/4611 |
| | | | | 623/17.16 |
| 2008/0133012 | A1 * | 6/2008 | McGuckin | A61F 2/441 |
| | | | | 623/17.12 |
| 2008/0208255 | A1 * | 8/2008 | Siegal | A61B 17/1757 |
| | | | | 606/246 |
| 2008/0221687 | A1 * | 9/2008 | Viker | A61F 2/4455 |
| | | | | 623/17.16 |
| 2008/0234827 | A1 * | 9/2008 | Schaller | A61B 17/8852 |
| | | | | 623/17.16 |
| 2008/0249628 | A1 * | 10/2008 | Altarac | A61F 2/4455 |
| | | | | 623/17.16 |
| 2008/0312743 | A1 * | 12/2008 | Vila | A61F 2/442 |
| | | | | 623/17.16 |
| 2009/0005871 | A1 * | 1/2009 | White | A61B 17/562 |
| | | | | 623/17.11 |
| 2009/0012616 | A1 * | 1/2009 | James | A61F 2/442 |
| | | | | 623/17.11 |
| 2009/0030423 | A1 * | 1/2009 | Puno | A61F 2/442 |
| | | | | 606/99 |
| 2009/0182431 | A1 * | 7/2009 | Butler | A61F 2/447 |
| | | | | 623/17.16 |
| 2009/0234454 | A1 * | 9/2009 | Siegal | A61B 17/7062 |
| | | | | 623/17.11 |
| 2009/0240335 | A1 * | 9/2009 | Arcenio | A61B 17/7094 |
| | | | | 623/17.16 |
| 2009/0306672 | A1 * | 12/2009 | Reindel | A61F 2/4611 |
| | | | | 606/90 |
| 2010/0185290 | A1 * | 7/2010 | Compton | A61B 17/7094 |
| | | | | 623/17.16 |
| 2011/0009969 | A1 * | 1/2011 | Puno | A61B 17/1757 |
| | | | | 623/17.12 |
| 2011/0029085 | A1 * | 2/2011 | Hynes | A61F 2/4611 |
| | | | | 623/17.16 |
| 2011/0046740 | A1 * | 2/2011 | Chen | A61F 2/4455 |
| | | | | 623/17.16 |
| 2011/0106260 | A1 * | 5/2011 | Laurence | A61F 2/4425 |
| | | | | 623/17.16 |
| 2011/0153021 | A1 * | 6/2011 | Diwan | A61B 1/0125 |
| | | | | 623/17.16 |
| 2011/0320000 | A1 * | 12/2011 | O'Neil | A61B 17/1659 |
| | | | | 623/17.16 |
| 2012/0029518 | A1 * | 2/2012 | Blackwell | A61B 17/1671 |
| | | | | 606/79 |
| 2012/0071980 | A1 * | 3/2012 | Purcell | A61F 2/4611 |
| | | | | 623/17.16 |
| 2012/0083887 | A1 * | 4/2012 | Purcell | A61F 2/447 |
| | | | | 623/17.16 |
| 2012/0136442 | A1 * | 5/2012 | Kleiner | A61F 2/4455 |
| | | | | 623/17.11 |
| 2012/0158140 | A1 * | 6/2012 | Miller | A61F 2/4425 |
| | | | | 623/17.11 |
| 2013/0023990 | A1 * | 1/2013 | Zipnick | A61F 2/442 |
| | | | | 623/17.16 |
| 2013/0035762 | A1 * | 2/2013 | Siegal | A61F 2/02 |
| | | | | 623/17.11 |
| 2013/0041469 | A1 * | 2/2013 | Phelps | A61F 2/4455 |
| | | | | 623/17.16 |
| 2013/0041471 | A1 * | 2/2013 | Siegal | A61F 2/442 |
| | | | | 623/17.16 |
| 2013/0079883 | A1 * | 3/2013 | Butler | A61F 2/4425 |
| | | | | 623/17.16 |
| 2013/0110239 | A1 * | 5/2013 | Siegal | A61B 17/7098 |
| | | | | 623/17.16 |
| 2013/0138214 | A1 * | 5/2013 | Greenhalgh | A61F 2/4455 |
| | | | | 623/17.16 |

(56) References Cited

U.S. PATENT DOCUMENTS

| | | | | |
|---|---|---|---|---|
| 2013/0144391 A1* | 6/2013 | Siegal | A61F 2/442 | 623/17.16 |
| 2013/0173004 A1* | 7/2013 | Greenhalgh | A61F 2/442 | 623/17.16 |
| 2013/0204370 A1* | 8/2013 | Danacioglu | A61F 2/4611 | 623/17.16 |
| 2013/0238098 A1* | 9/2013 | Schaller | A61B 17/8852 | 623/17.16 |
| 2013/0325128 A1* | 12/2013 | Perloff | A61F 2/4455 | 623/17.16 |
| 2014/0039625 A1* | 2/2014 | To | A61F 2/4455 | 623/17.16 |
| 2014/0052253 A1* | 2/2014 | Perloff | A61F 2/4425 | 623/17.15 |
| 2014/0058513 A1* | 2/2014 | Gahman | A61F 2/442 | 623/17.16 |
| 2014/0243980 A1* | 8/2014 | Sack | A61F 2/442 | 623/17.11 |
| 2014/0277481 A1* | 9/2014 | Lee | A61F 2/4455 | 623/17.16 |
| 2014/0277499 A1* | 9/2014 | Ainsworth | A61F 2/4455 | 623/17.16 |
| 2014/0358246 A1* | 12/2014 | Levy | A61F 2/4455 | 623/23.47 |
| 2014/0379086 A1* | 12/2014 | Elahinia | A61F 2/4465 | 623/17.16 |
| 2015/0025634 A1* | 1/2015 | Boehm | A61F 2/4425 | 623/17.15 |
| 2015/0173910 A1* | 6/2015 | Siegal | A61F 2/442 | 623/17.16 |
| 2015/0230929 A1* | 8/2015 | Lorio | A61F 2/4611 | 623/17.16 |
| 2015/0250518 A1* | 9/2015 | Chirico | A61B 17/70 | 623/17.11 |

FOREIGN PATENT DOCUMENTS

| | | |
|---|---|---|
| JP | 2010509985 A | 4/2010 |
| JP | 2010538684 A | 12/2010 |
| WO | 00/71043 A1 | 11/2000 |
| WO | 2007022194 A2 | 2/2007 |
| WO | 2008124739 A1 | 10/2008 |
| WO | 2011123439 A2 | 10/2011 |

OTHER PUBLICATIONS

Japanese Office Action, Application No. JP 2014-531958, dated May 23, 2016.

* cited by examiner

EXPANDABLE INTER-VERTEBRAL CAGE AND METHOD OF INSTALLING SAME

RELATED APPLICATIONS

This is a national stage application filed under 37 C.F.R. §1.371 of international application PCT/US12/56297, filed under the authority of the Patent Cooperation Treaty on Sep. 20, 2012, which claims priority to United States Provisional Application Ser. No. 61/536,744, filed under 35 U.S.C. §111(b) on Sep. 20, 2011. The entire disclosures of all priority applications are incorporated herein by reference.

BACKGROUND OF THE INVENTION

This invention relates in general to the treatment of diseases of the spine using inter-vertebral devices and implantation methods. In particular, this invention relates to an automatically self-expanding inter-vertebral cage that can enter into a cavity through a small opening and automatically acquire any desired form as a result of being either released from an installation tool or from being exposed to environmental conditions, such as temperature, moisture, light, magnetic field, electric field, pressure, etc. (or the lack thereof). More particularly, the self-expanding inter-vertebral cage of this invention can utilize shape memory alloy materials to accomplish the automatic activation.

One of the most common causes for disability in people aged forty-five to sixty-five is pain in the lower back. Often, this is caused by compression of an inter-vertebral disc, which creates pressure on nerves extending from the spinal cord. Decompression spinal fusion procedures (also called inter-body fusion) are an effective means to reduce and, in some cases, eliminate numbness, weakness, and pain stemming from numerous medical conditions including, but not limited to, disc degeneration, spondylolisthesis, and disc herniation. There are also other causes of back pain, such as facet joint arthrosis, slipping of one vertebrae over another, deformity, and the like.

In cases of chronic back pain or weakness, spinal fusion procedures are usually recommended as a last resort. Procedures such as these share a relatively high risk of injury that coincides with the rewards of decompression of nerves and relief from debilitating pain. Thus, it is usually suggested that conservative management procedures, such as physical therapy, non-steroidal anti-inflammatory drugs, pain management, and muscle relaxing drugs be attempted and proven to unsuccessful in the treatment of the pain for at least six months before any surgical procedure is performed.

Although decompression spinal fusion procedures often succeed in removing the nerve pain, the pain related to instability between the two vertebrae often requires stabilization of the vertebrae level. Because the highest levels of stress and degradation of inter-vertebral bodies occurs in the lower (or "lumbar") spine, this area is the focus of most fusion procedures, including posterior lumbar interbody fusion (PLIF), anterior lumbar interbody fusion (ALIF), transforaminal lumbar interbody fusion (TLIF), far lateral lumbar interbody fusion (FLLIF), and, more recently, extreme lateral interbody fusion (XLIF). The names of these surgical procedures denote the anatomical direction from which they are inserted. Each of these procedural approaches for implanting interbody fusion devices has its own set of advantages and disadvantages. As will be explained in greater detail below, this invention can be practiced using any of these techniques, as well as other techniques, in particular minimally invasive techniques.

A typical lumbar fusion device ranges in height from 10 mm to 20 mm based upon which motion segment is to be fused, as well as patient-specific measurements. The PLIF is one of the most flexible procedures, being able to access all lumbar and sacral motion segments. However, it is also one of the most dangerous procedures because of its close proximity to the spinal cord. Because of that, it has been determined that a minimally invasive device and procedure would be best suited for application in this surgical approach. The self-expanding inter-vertebral cage described and illustrated herein requires a much smaller incision compared to existing full-sized cages, which allows the cage to be elongated prior to insertion. As a result, the cage of this invention can be installed through a much smaller incision than previously available, an incision having a size that is approximately equal to a width of the elongated cage.

SUMMARY OF THE INVENTION

This invention relates to a novel self-expanding inter-vertebral cage that utilizes shape memory alloy materials or other means for automatic activation from an initial extended orientation to a final installed orientation. The cage can be inserted between the vertebral bodies through a relatively small incision in the annulus fibrosus. Upon entry into the inter-vertebral space, the shape memory alloy material or other mechanism can activate the inter-vertebral cage, causing it to acquire a desired form. Once this desired form is reached, the distraction of the vertebral bodies will be released, and the cage will be put under a compressive load. Thus, the cage will act as a load-bearing, stabilizing structure that is left within the spine to support fusion.

The inter-vertebral cage of this invention can include several interconnected cage sections that act as load bearing structures. Adjacent ones of the cage sections can be connected to one another by hinge elements formed from shape memory alloy materials, which can be in a torsionally stressed condition and such that they stay in place on their own. Alternatively, the hinge elements may be attached to the respective cage sections by a butt weld or other mechanism. The hinge elements may be bent so as to allow for more active wire within the hinge element such that a larger wire or tube may be used to provide higher restoring torque. The shape memory alloy material can withstand higher deformation than standard engineering metals and can also provide a constant force/torque over a wide range of linear/angular deformation. These properties will be utilized in creating a cage which will automatically activate into and hold a desired orientation during and after installation. The cage will be constructed in its desired shape with a small amount of pre-torque in the hinge element. Once assembled, the cage will assume the initial extended shape, causing the hinge elements to be torsionally stressed. The cage will then be placed within an installation device, such as an endoscope, which will hold the deformed shape until the cage is inserted within an inter-vertebral space. In doing this, the actuation of the shape memory/superelastic alloy will close an extended cage into a desired shape, preferably defining an open cavity for the placement of bone graft material. Following the placement of the graft material, a final securing screw can be applied to secure the end sections of the inter-vertebral cage and thereby close same. Also, the cage sections may have pyramidal-shaped protrusions or other features provided on the top and/or bottom surfaces thereof to facilitate proper securing of the cage as a whole to the adjacent vertebral bodies.

Current expandable cages that utilize a standard hinge usually require a secondary activation force either during or after installation, such as by tightening a screw or by manually pushing walls of the cage from the center. This secondary activation force often necessitates more time and effort during the surgical procedure and, thus, increases the risk of complications and infection. Also, these cages generally require a larger incision than the proposed design because they are closed structures that define permanent cavities within the activation device. Other known cages have been designed utilizing shape memory alloy materials, but they similarly usually require a larger incision due to their "closed loop" design. Where a standard expandable cage would have all of the walls attached prior to insertion, the proposed design has an "open loop" design so that a much smaller horizontal profile is provided.

The installation of the inter-vertebral cage of this invention can be accomplished directly by means of a minimally invasive installation technique. Alternatively, a new technique is proposed for implanting this cage using an endoscope. The endoscope method is still minimally invasive in nature, but would allow direct visualization of every stage of the procedure by the surgeon, thereby reducing the number of potential complications. The configuration of the cage can be designed in such a way that it can be inserted by any known minimally invasive technique or by new techniques. The cage of this invention is advantageous over known cages in that it give optimal placement in the inter-vertebral space.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
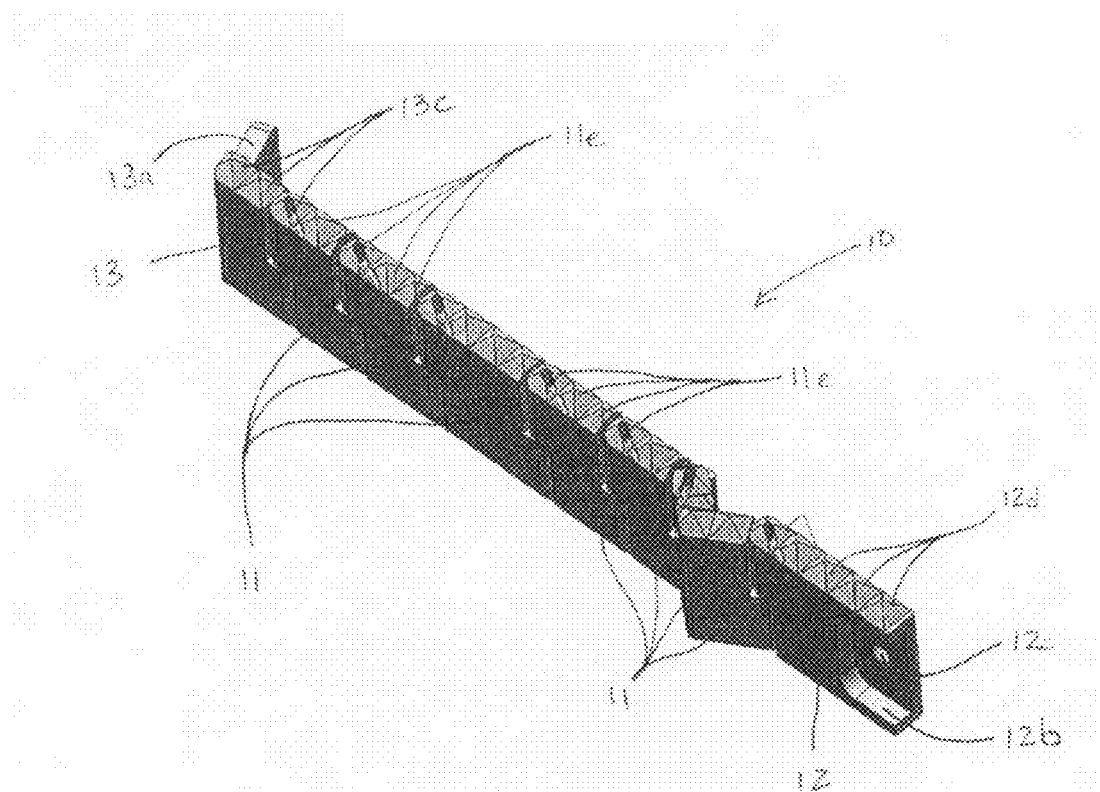
FIG. 1 is a perspective view of a first embodiment of an inter-vertebral cage in accordance with this invention, shown in an initial extended orientation.
Figure 2:
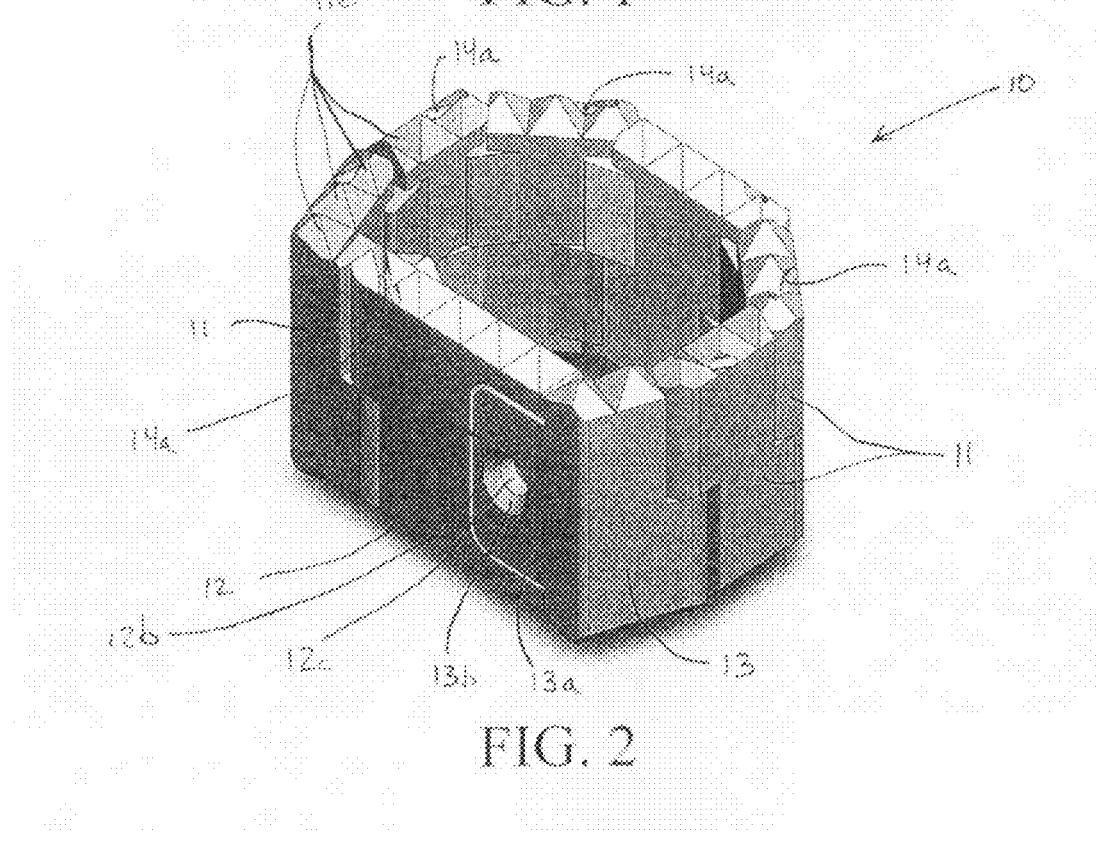
FIG. 2 is an enlarged perspective view of the inter-vertebral cage illustrated in FIG. 1 shown in a final installed orientation.
Figure 3:
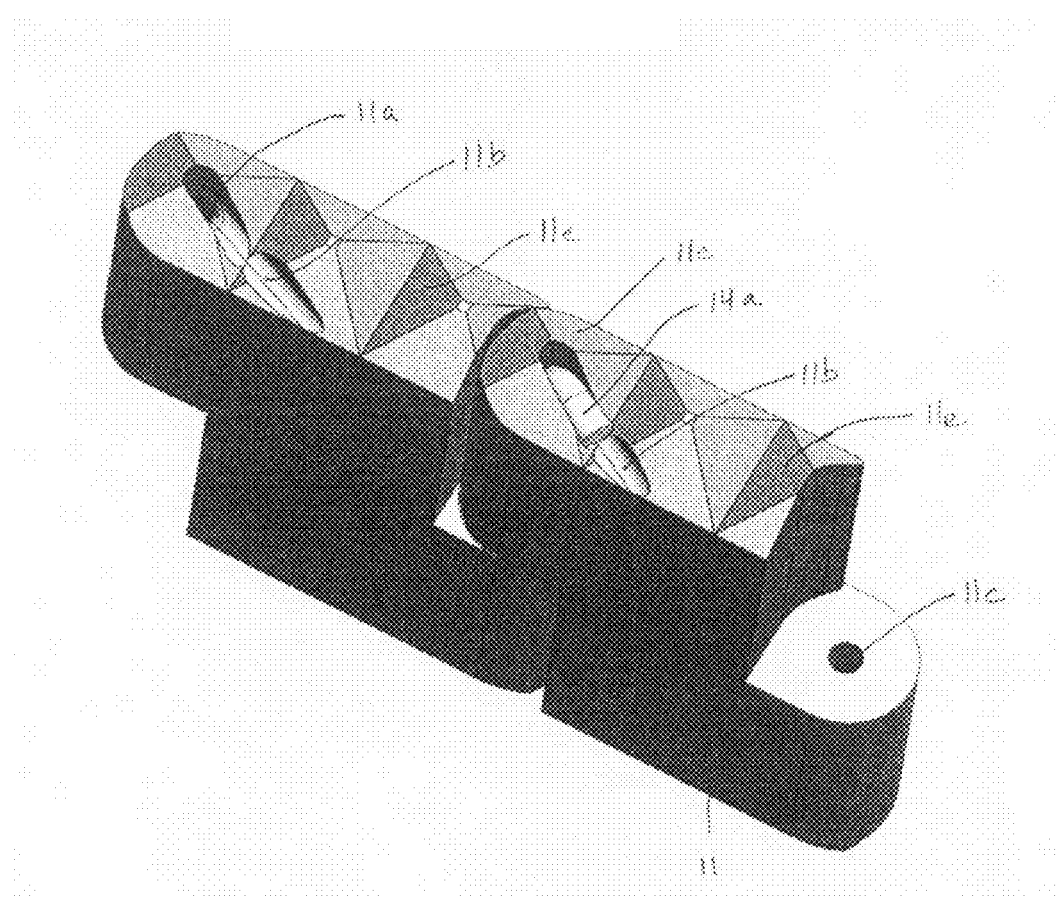
FIG. 3 is an enlarged perspective view of a portion of the first embodiment of the inter-vertebral cage illustrated in FIG. 1 showing two cage sections having a hinge element connected therebetween.

Referring now to the drawings, there is illustrated in FIGS. 1 through 3 a first embodiment of an inter-vertebral cage, indicated generally at 10, in accordance with this invention. In FIG. 1, the inter-vertebral cage 10 is shown in an initial extended orientation for insertion into a space provided within an inter-vertebral disc that is disposed between two vertebrae of a spine in a manner that will be described in detail below. Following such insertion, the inter-vertebral cage 10 can be moved from this initial extended orientation to a final installed orientation (illustrated in FIG. 2) for use. The manner in which the cage 10 is moved from the initial extended orientation to the final installed orientation will be explained in detail below.

The first embodiment of the inter-vertebral cage 10 includes a plurality of individual cage sections 11, a first end section 12, and a second end section 13. In the illustrated embodiment, the inter-vertebral cage 10 includes six of the individual cage sections 11, although a greater or lesser number may be provided as desired. As best shown in FIG. 3, each of the cage sections 11 has a first aperture 11a formed therethrough and a first recess 11b that extends from the first aperture 11a externally along an upper surface thereof. Similarly, each of the cage sections 11 also has a second aperture 11c formed therethrough and a second recess (see FIG. 9) that extends from the second aperture 11c externally along a lower surface thereof. The purposes of the apertures 11a and 11c and the recesses 11b will be explained below. The cage sections 11 are shaped such that the first aperture 11a of one of the cage sections 11 can be aligned with the second aperture 11c of an adjacent one of the cage sections 11, as shown in FIGS. 1, 2, and 3.

The upper and lower surfaces of some or all of the cage sections 11 may be formed having retaining structures 11e, also for a purpose that will be explained below. In the illustrated embodiment, the upper and lower surfaces of the cage sections 11 are formed having retaining structures 11e that are shaped as pyramidal protrusions, although the retaining structures may be formed having any desired shape or combination of shapes.

The first end section 12 has an aperture (not shown) formed therethrough that is similar to the apertures 11a and 11c of the adjacent cage section 11. The aperture formed through the first end section 12 can be aligned with one of the apertures 11a or 11c of the adjacent cage section 11 so that the first second section 12 can be connected to the adjacent cage section 11 in the same manner as the two cage sections 11 illustrated in FIG. 3. The first end section 12 may be provided with a recess 12b having a locking structure (such as an opening 12c formed therethrough) for purposes that will be explained below. Lastly, the first end section 12 may also be provided with one or more retaining structures 12d on the upper and lower surfaces thereof for a purpose that will be explained below.

Similarly, the second end section 13 also has an aperture (not shown) formed therethrough that is similar to the apertures 11a and 11c of the adjacent cage section 11. The aperture formed through the second end section 13 can be aligned with one of the apertures 11a or 11c of the adjacent cage section 11 so that the second end section 13 can be connected to the adjacent cage section 11 in the same manner as the two cage sections 11 illustrated in FIG. 3. The second end section 13 may be provided with a tab 13a having a locking structure (such as an opening 13b formed therethrough) for purposes that will be explained below. Lastly, the second end section 13 may also be provided with one or more retaining structures 13c on the upper and lower surfaces thereof for a purpose that will be explained below.

The cage sections 11, the first end section 12, and the second end section 13 can be formed from any desired material or combination of materials. For example, these sections 11, 12, and 13 can be formed from a titanium alloy material, such as $Ti_6Al_4V$, which has proven efficacy, biocompatibility, cost-effectiveness, strength, and a modulus that is closer to bone than that of stainless steel. This material also allows easy application of bio-conductive material coatings, as well as colored coatings that may be utilized to easily distinguish various cage sizes. Easy recognition of differently-sized cages in a surgical setting reduces confusion and, thus, minimizes procedural time and error associated with placement of an incorrectly sized cage.

Figure 4:
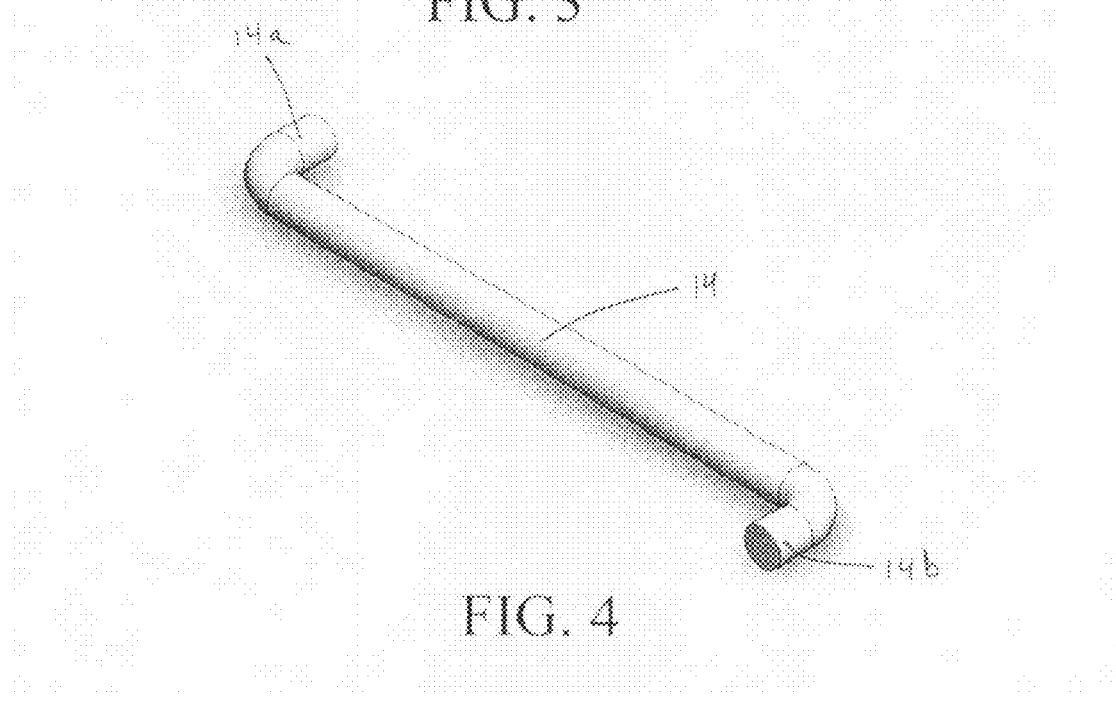
FIG. 4 is a further enlarged perspective view of the hinge element illustrated in FIG. 3 shown in a torsionally stressed condition as it would appear when the inter-vertebral cage is in the initial extended orientation shown in FIGS. 1 and 3.

The cage sections 11, the first end section 12, and the second end section 13 are connected together by hinge elements 14, one of which is illustrated in detail in FIG. 4. As shown therein, the hinge elements 14 may be embodied as wire-shaped members, each including a central body having a first end 14a and a second end 14b extending therefrom at angles. In the illustrated embodiment, the first end 14a and the second end 14b are bent so as to extend generally perpendicularly from the central body of the hinge element 14, although such is not required. Each of the hinge elements 14 can be used to connect adjacent ones of the cage sections 11, the first end section 12, and the second end section 13 together as shown in FIGS. 1, 2, and 3. Referring back to FIG. 3, the central body of the hinge element 14 extends through the aligned apertures 11a and 11c of adjacent ones of the cage sections 11, thereby allowing such cage sections 11 to pivot relative to one another. At the same time, the first end 14a of the hinge element 14 is received within the recess 11b formed in the upper surface of a first one of the cage sections 11, while the second end 14b of the hinge element 14 is received within the recess (not shown) formed in the lower surface of a second one of the cage sections 11. The hinge elements 14 can be used to connect the first and second end sections 12 and 13 to adjacent ones of the cage sections 11 in a similar manner.

The hinge elements 14 are adapted to urge the adjacent ones of the cage sections 11 and the first and second end sections 12 and 13 to extend at an angle relative to one another (i.e., out of the initial extended orientation illustrated in FIG. 1). In particular, the hinge elements 14 are adapted to urge the adjacent ones of the cage sections 11 and the first and second end sections 12 and 13 toward the installed orientation illustrated in FIG. 2, wherein the first and second end sections 12 and 13 are in contact with or are disposed adjacent to one another so as to define a generally closed interior. To accomplish this, when a hinge element 14 is installed on the cage sections 11 as shown in FIG. 3 and the cage 10 is in the initial extended orientation illustrated in FIG. 1, the hinge element 14 can be disposed in a torsionally stressed condition, as shown in FIG. 4. In the illustrated embodiment, the torsionally stressed condition is characterized when the first and second ends 14a and 14b of the hinge element 14 extend generally parallel to one another in opposite directions (i.e., at an approximately 180° angle), whereas in a torsionally unstressed (or at least torsionally lesser stressed) condition, the first and second ends 14a and 14b of the hinge element 14 extend at a lesser angle relative to one another. Thus, when the cage 10 is deployed from an installation device, the hinge element 14 relieves the torsional stresses by moving the cage sections 11 from the initial extended orientation illustrated in FIG. 1 toward the final installed orientation illustrated in FIG. 2, wherein adjacent ones of the cage sections 11 are oriented at angles relative to one another.

In the installed orientation, it is preferable (but not required) that the first and second end sections 12 and 13 of the cage 10 be disposed either in direct contact or adjacent to one another. As shown in FIG. 2, the first and second end sections 12 and 13 of the cage 10 are preferably oriented such that the tab 13a of the second end section 13 is received within the recess 12b of the first end section 12. When so oriented, the locking structures of the first and second end sections 12 and 13 (in the illustrated embodiment, the openings 12c and 13b) are aligned with one another, again as shown in FIG. 2. The first and second end sections 12 and 13 of the cage 10 may be selectively retained together in the manner merely by the cooperation of the tab 13a with the recess 12b. Alternatively, a fastener (not shown) or other structure may extend through the aligned openings 12c and 13b or otherwise cooperate with the first and second end sections 12 and 13 to positively retain them together.

Each of the hinge elements 14 may, if desired, be formed from a shape memory alloy material. Shape memory alloy materials are metals having two distinct properties, namely, shape memory effect and superelasticity. The shape memory effect stems from the thermo-mechanical coupling of the metal. One of the most common uses of this coupling for the shape memory effect is the deformation of the material by inducing a stress, then the recovery of the strains through thermal cycling. This is possibly due to the fact that the thermo-mechanical coupling stems from a solid-state transformation of the crystalline structure, which takes place with a moderate temperature variation. In the case of shape memory effect, the material at low temperatures will transform from a twinned martensitic phase to a detwinned (also known as deformed) martensitic phase. Upon heating above a specific temperature (called the austenite finish temperature), the material will transform to the austenitic phase, following which a cooling process will return the material to the original twinned martensite phase. The other distinct property of this material, superelasticity, is exhibited when the material is at a temperature above the aforementioned austenite finish temperature. At this temperature, the material is in a fully austenitic phase, and stress causes the material to change to martensite and then return to austenite upon loading and unloading, respectively.

For example, nitinol may be used to form the hinge elements 14. This material is readily available from several manufacturers and has already seen usage in medical devices. The high levels of recoverable strain in this material allow for the hinge elements 14 to recover relative rotations of up to 80° with no spring-back force necessary for implementation of this design. Nitinol hinge elements allow for immediate, unassisted movement of one cage segment 11 relative to another until the final installed orientation is achieved and a locking fixator is placed. This unassisted movement means that the cage does not need to be a larger, completely linked chain that requires a secondary procedure to expand it to its final size, as described above.

Devices such as torsional springs with a recovery angle of this magnitude are difficult to manufacture for a device such as this with a vertical height ranging only from 10 mm to 20 mm. Also, spring steel utilized for the development of these devices may show a certain level of irreversible strain, which could allow for undesirable movement in the hinge mechanism. Another key difference between a torsional spring and a nitinol hinge is the relationship between force and displacement. Even if it were relatively feasible to manufacture a device that could obtain 80° of rotation with only 10 mm of length, a standard torsion spring would show a linear relationship between force (torque) and displacement (angle of rotation), meaning that as the device is released, the level of torque would linearly decrease as the angle decreased. This would mean that when the relative angle between segments was at a minimum in the final installed orientation, the cage would be easier to move because of less opposition from the torsional spring. On the other hand, a nitinol or shape memory alloy hinge can be preloaded such that loading or unloading of the material (increasing or decreasing of the angle in this case) would remain at a relatively consistent force/torque level within a certain range of motion. Based on calculations from known stress-strain curves of nitinol, one exemplary range of 0.016" to 0.030" diameter wire can be used for the hinge elements 14 in this design.

Figure 5:
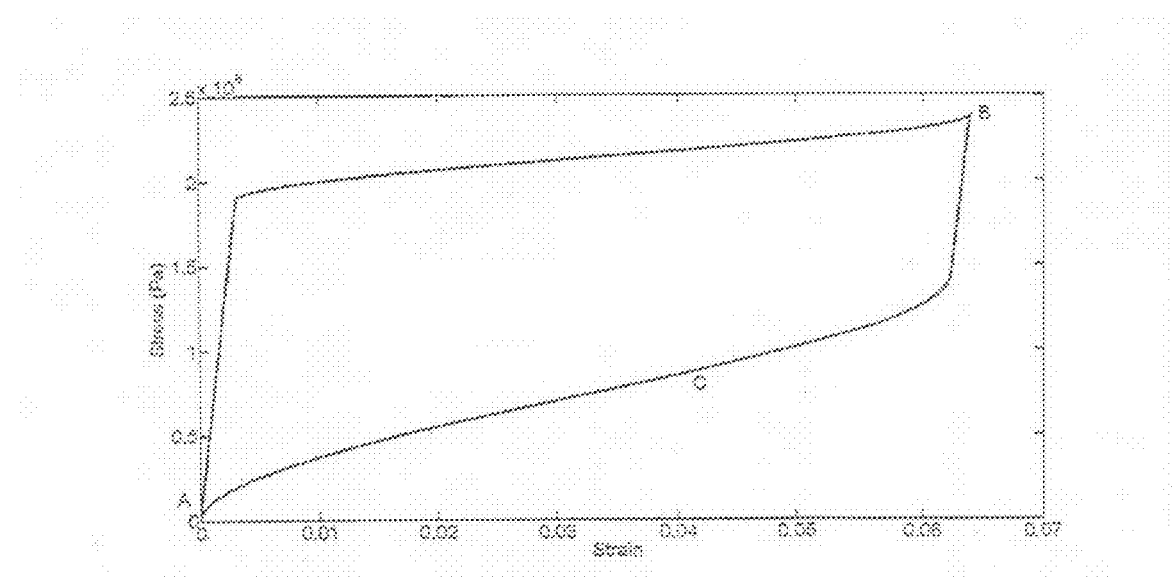
FIG. 5 is a graph that illustrates an envisioned stress strain path for the hinge element illustrated in FIG. 4.
Figures 6, 7, 8:
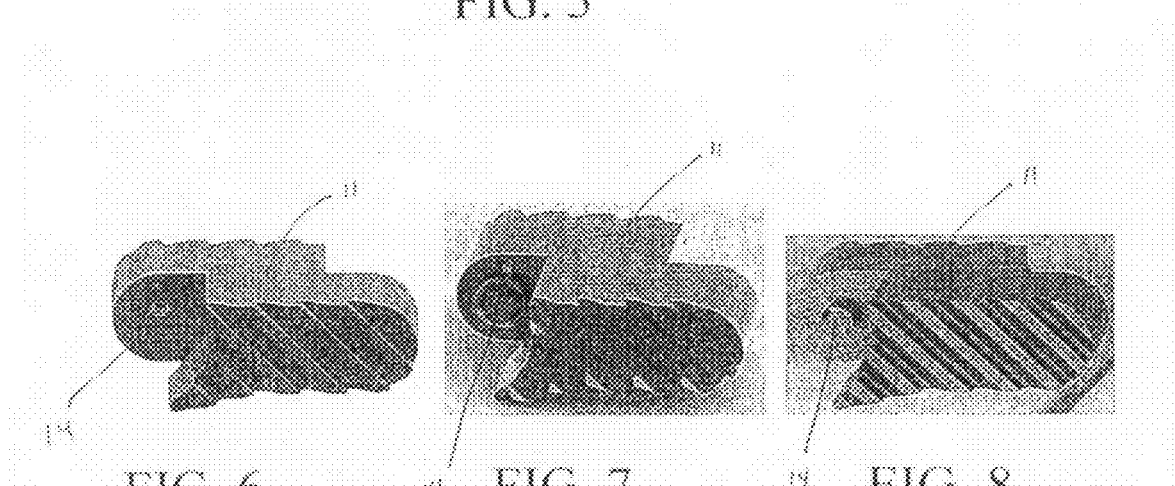
FIGS. 6, 7, and 8 schematically illustrate hinge positions corresponding to points A, B, and C in the graph of FIG. 5.

The envisioned stress strain path for the hinge element 14 is shown in FIG. 5, while the corresponding hinge positions are shown schematically in FIGS. 6, 7, and 8. As shown therein, the cage section 11 will initially be unloaded (as shown in FIG. 5 and at point A in FIG. 5. The other cage section 11 is then added on, and a pre-torque is given to the hinge element 14 (as shown in FIG. 7 and from point A to point B in FIG. 5. Then, when unloading (as would occur when the cage 10 is deployed as described below), the hinge element takes the form shown in FIG. 8 and from point B to point C in FIG. 5. This will take advantage of another property of the shape memory allow material, namely, the bias-stiffness. The geometry of the hinge element 14 is not limited to the specific embodiment shown in FIGS. 6, 7, and 8. For example, the hinge element 14 can have a hexagonal or other non-circular cross-sectional shape. Another envisioned embodiment of this invention is to include hard mechanical stops into the cage section design to insure proper actuation and deployment.

Figure 9:
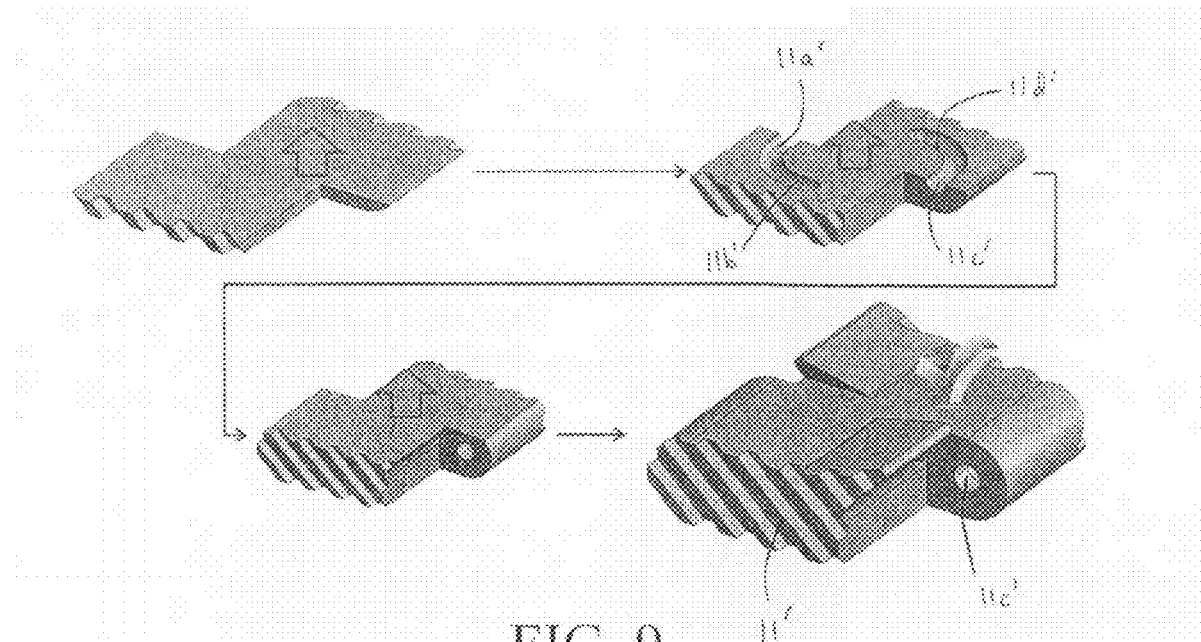
FIG. 9 illustrates the sequence of steps in a method for manufacturing one of the cage sections illustrated in FIGS. 1, 2, and 3.
Figures 10, 11:
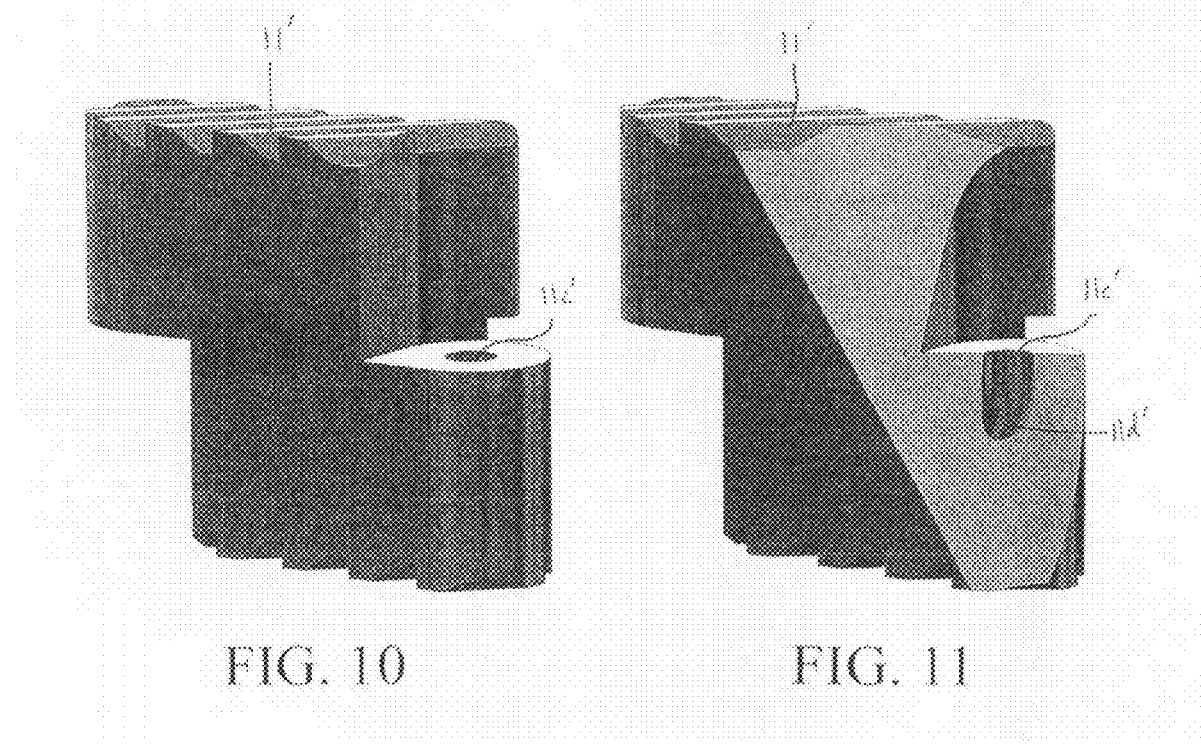
FIG. 10 is an enlarged perspective view of one of the cage sections manufactured in accordance with the method illustrated in FIG. 9.
FIG. 11 is an enlarged perspective view, partially in cross section, of a portion of the cage section shown in FIG. 10.

Some or all of the cage sections 11, the first end section 12, and the second end section 13 may be manufactured by an additive manufacturing process, which is schematically illustrated in FIG. 9. As shown therein, each of the sections 11, 12, and 13 are manufactured layer by layer until the entire part is realized. Using this process, however, that a modified version of the cage sections 11' can be formed having apertures 11a' and 11c' and, more importantly, recesses 11b' and 11d' formed internally therein, thereby preventing any portions of the hinge elements 14 from being exposed externally. This modified cage section 11' design eliminates any chance that any parts of the first and second end portions 14a and 14b of the hinge element 14 may catch or tear tissue during installation and use. FIGS. 10 and 11 illustrate one of the modified version of the cage sections 11' manufactured in accordance with the method illustrated in FIG. 9.

Figure 12:
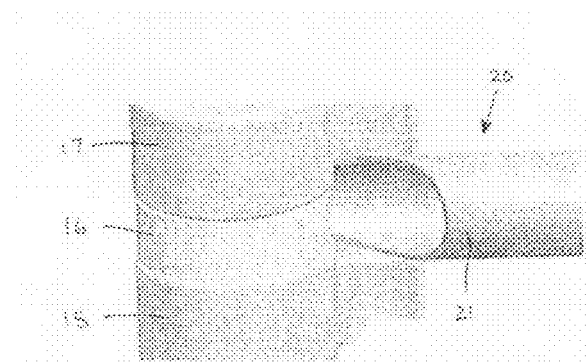
FIGS. 12 through 18 are perspective views of a first embodiment of an installation device including an endoscope being used in accordance with a first minimally invasive method of this invention to install the inter-vertebral cage illustrated in FIG. 1 within an inter-vertebral disc disposed between adjacent vertebrae.

The method of installation and the automatic deployment and operation of the inter-vertebral cage 10 are illustrated in detail in FIGS. 12 through 18. As shown therein, a damaged inter-vertebral disc 15 is disposed between adjacent vertebrae 16 and 17 of a spine, and a first embodiment of an installation device, indicated generally at 20, can be used to install the inter-vertebral cage 10 illustrated in FIG. 1 within the damaged inter-vertebral disc 15. The first embodiment of the installation device 20 may, if desired, include a hollow dilator 21 that is initially positioned adjacent to an annulus fibrosus of the inter-vertebral disc 15, as shown in FIG. 12 (the annulus fibrosus being the strong wrapping that makes up the outside portion of the damaged inter-vertebral disc 15). The dilator 21 can be positioned in this manner using any conventional procedure. For example, a guide wire (not shown) can be inserted using any of the desired approaches mentioned above (i.e., the PLIF, ALIF, TLIF, and FLLIF approaches, for example). The damaged inter-vertebral disc 15 can be identified by injecting a dye in a conventional manner. Thereafter, a guide rod (not shown) or the dilator 21 itself can be inserted about of the guide wire to the desired location.

Figure 13:
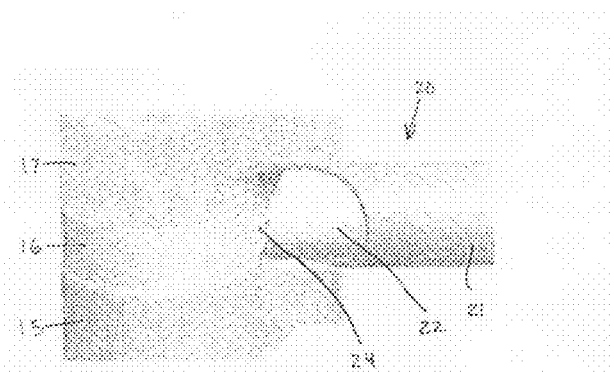
Figure 19:
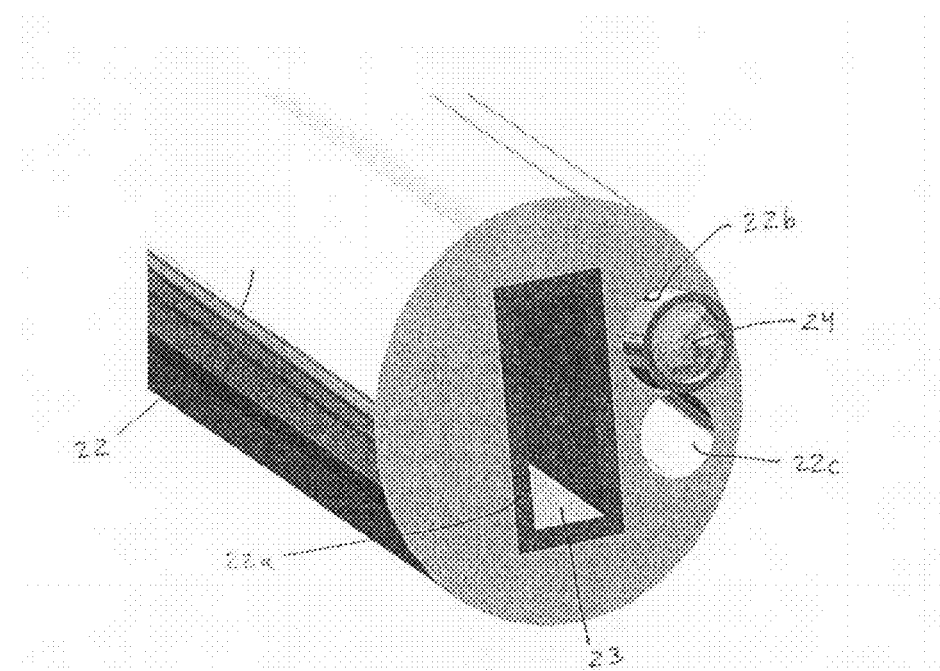
FIGS. 19 and 20 are enlarged perspective views of an end portion of the first embodiment of the endoscope illustrated in FIGS. 12 through 18.
Figure 20:
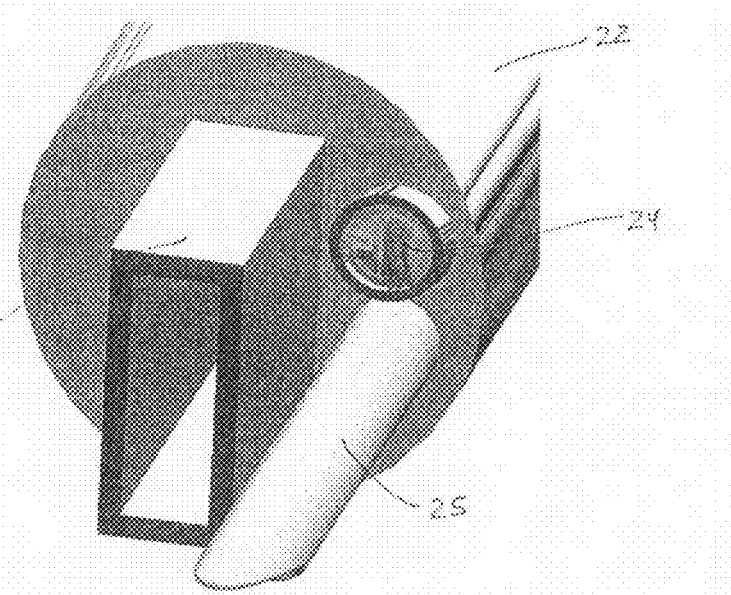

Then, as shown in FIG. 13, an endoscope 22 is inserted through the dilator 21 such that the leading end thereof is positioned adjacent to the annulus fibrosus of the damaged inter-vertebral disc 15. The structure of the endoscope 22 is illustrated in detail in FIGS. 19 and 20. As shown therein, the endoscope 22 includes a first opening 22a that supports a cartridge 23, a second opening 22b that supports a conventional camera lens 24, and a third opening 22c that can provide access to any other desired instrument, such as a conventional cannula 25 as shown in FIG. 20. The illustrated first opening 22a is relatively large and rectangularly-shaped, as is the cartridge 23 supported therein. The rectangularly-shaped cartridge 23 can help in distortion of the space of the damaged inter-vertebral disc 15 and functions, as described further below, as a carrier of cage 10 prior to deployment and operation. However, the first opening 22a and the cartridge 23 may have any desired sizes or shapes, or combinations thereof. Likewise, the second and third openings 22b and 22c, as well as any devices supported therein, may have any desired sizes or shapes, or combinations thereof. The purposes for the cartridge 23 and the camera 24 will be explained below.

Figure 14:
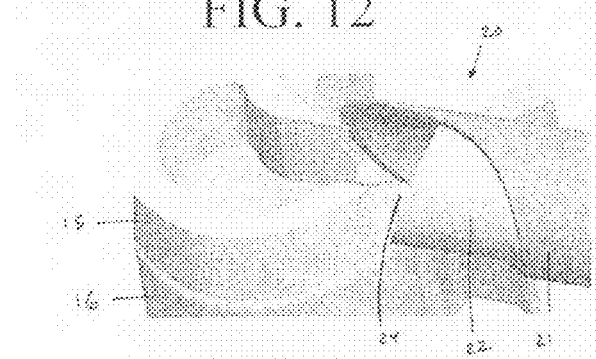

As mentioned above, the dilator 21 is initially positioned adjacent to the annulus fibrosus of the damaged inter-vertebral disc 15. If desired, the camera 24 can be used to facilitate such positioning. Thereafter, a small portion of the annulus fibrosus of the damaged inter-vertebral disc 15 (as well as the nucleus of the disc 15 contained within the annulus fibrosus) is removed in a conventional manner, as shown in FIG. 14. For example, the removal of the small portion of the annulus fibrosus can be accomplished by a conventional surgical tool (not shown) that is inserted through the third opening 22c formed through the endoscope 22 and subsequently retracted therefrom (the third opening 22c can be used to facilitate access to the damaged inter-vertebral disc 15 by any other surgical or other type of instrument).

Figure 15:
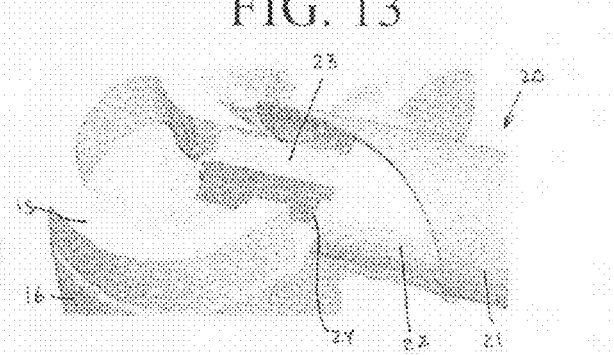
Figure 21:
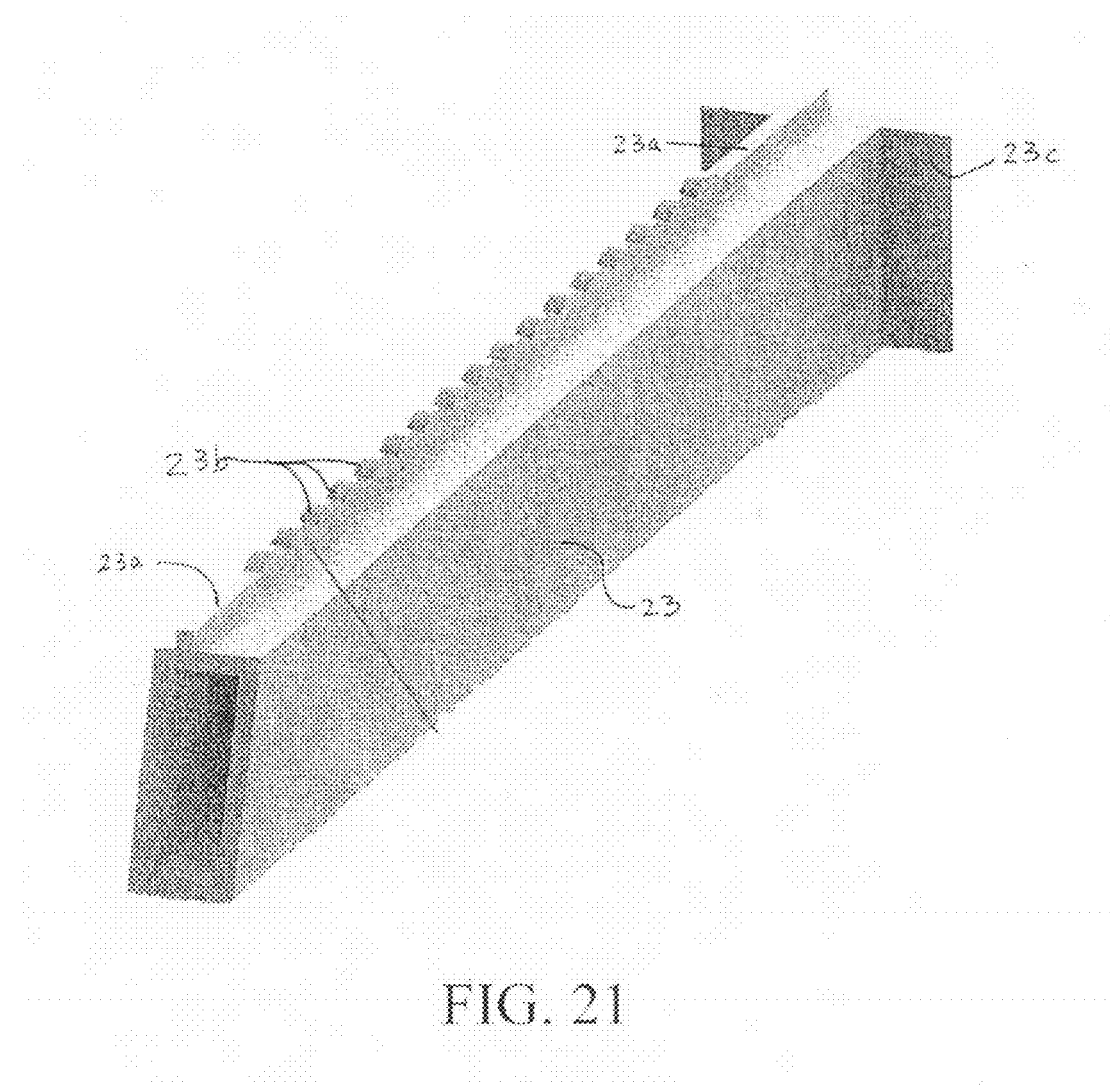
FIG. 21 is an enlarged perspective view of a cartridge portion of the first embodiment of the endoscope illustrated in FIGS. 12 through 19.
Figure 22:
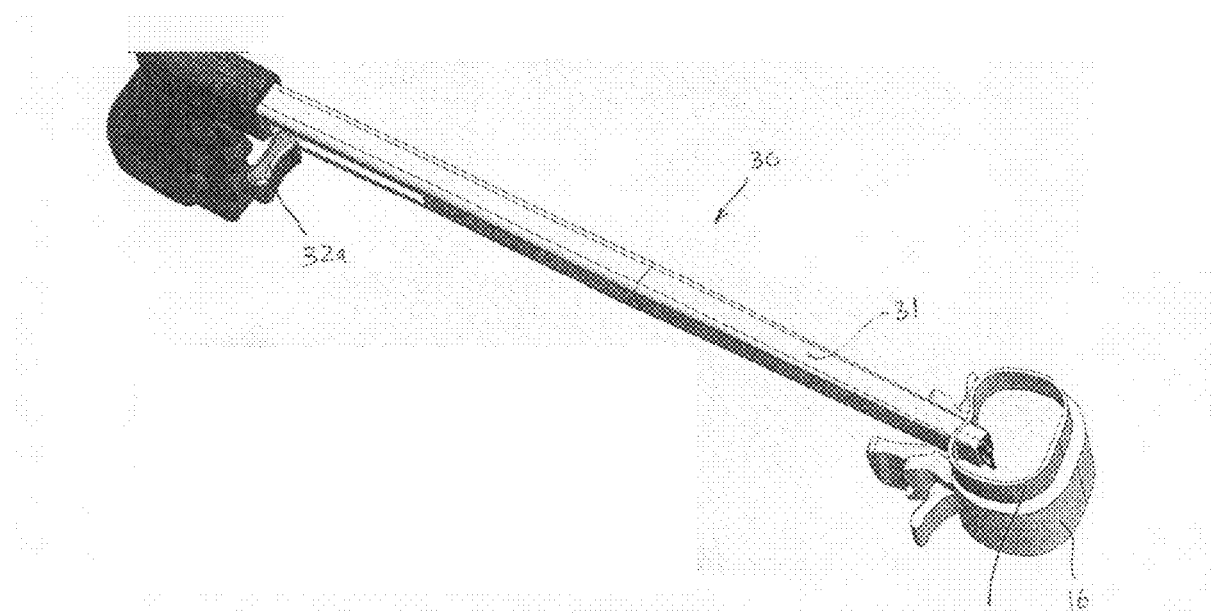
FIGS. 22 through 32 are perspective views of a second embodiment of an installation device including an endoscope being used in accordance with a second minimally invasive method of this invention to install the inter-vertebral cage illustrated in FIG. 1 within an inter-vertebral disc disposed between adjacent vertebrae.

Next, the cartridge 23 is extended from the leading end of the endoscope, as shown in FIG. 15. The structure of the cartridge 23 is illustrated in detail in FIG. 21. As shown therein, the illustrated cartridge 23 includes a locator ridge 23a provided thereon. The locator ridge 23a cooperates with a corresponding locator recess (not shown) provided on the endoscope 22 such that the cartridge 23 may only be inserted within the endoscope 22 in a single, predetermined orientation relative thereto. This single, predetermined orientation can help assure that the deployment of the cage 10 (as described below) is expected and correct. The locator ridge 23a may be omitted from the cartridge 23 if desired.

The illustrated cartridge 23 also has a plurality of teeth 23b formed on an outer surface thereof. The plurality of teeth 23b are provided to facilitate movement of the cartridge relative to the endoscope 22. For example, the plurality of teeth 23b may mesh with teeth provided on a rotatable gear (not shown) that is operable by the surgeon (either manually or by means of a powered motor) to move the cartridge 23 relative to the endoscope 22 and/or to lock the cartridge 23 in a predetermined position relative to the endoscope 22. It will be appreciated that the teeth 23b may themselves function as the locator ridge 23a. Also, the plurality of teeth 23b may be omitted from the cartridge 23 if desired.

The illustrated cartridge 23 is further provided with a stop flange 23b at the outermost end thereof. The stop flange 23b may be provided to positively limit the amount by which the cartridge 23 may be moved relative to the endoscope 22. It will also be appreciated that the stop flange 23b may also be omitted from the cartridge 23 if desired.

Figure 16:
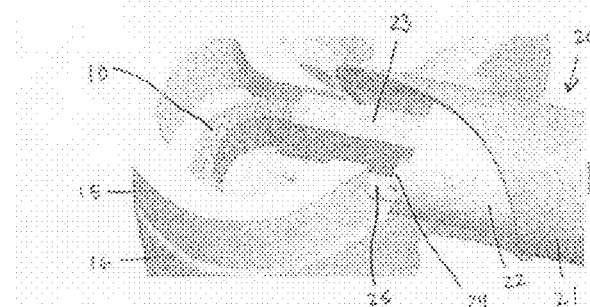

In the next step of the installation method illustrated in FIG. 16, the cage 10 is moved through the hollow interior of the cartridge 23 and extended from the leading end thereof into the interior of the damaged inter-vertebral disc 15.

Preferably, the cage 10 is preloaded within the cartridge 23, although such is not required. As the leading end of the cage 10 enters the space between the vertebrae 16 and 17, it automatically begins to curl out of the initial extended orientation and toward the final installed orientation under the urging of the hinge elements 14. As also shown in FIG. 16, the cannula 25 can be extended from the leading end of the endoscope 22. Preferably, the cannula 25 is extended from the endoscope 22 when the cage 10 is almost fully delivered within the interior of the damaged inter-vertebral disc 15. However, the cannula 25 can be extended from the endoscope 22 at any desired point in this process.

Figure 17:
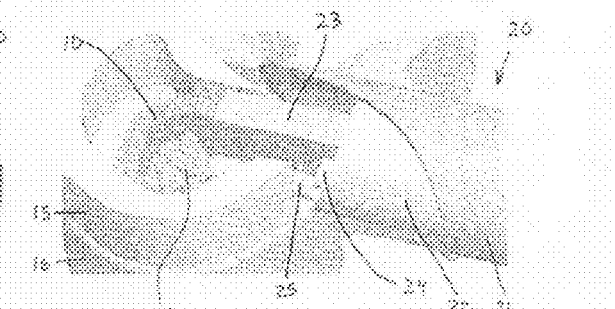

As shown in FIG. 17, the cannula 25 can be used to inject a bone graft or other material 26 into the interior space of the damaged inter-vertebral disc 15. Preferably, such material 26 is injected within the space defined by the cage 10 when it is at or near its installed orientation, although such is not required. If desired, the material can be injected at other areas of the interior of the damaged inter-vertebral disc 15. When a sufficient amount of the material 26 has been injected, the cannula 25 can be removed from the endoscope 22. The insertion of the cage 10 within the interior of the damaged inter-vertebral disc 15 is continued until the cage 10 is deployed in its fully installed orientation. At that point, the cartridge 23 can be retracted within the endoscope 22.

Figure 18:
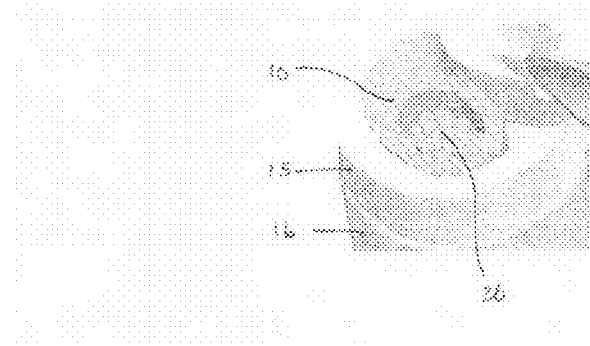

If desired, the above-mentioned fastener (not shown) can be inserted through the third opening 22c of the endoscope 22 and installed in the aligned openings 12c and 13b of the first and second end sections 12 and 13, respectively, of the cage 10. This action, along with all of the other actions described above, can be facilitated by means of the camera 24, which can provide the surgeon with a direct view of the interior of the damaged inter-vertebral disc 15. The endoscope 22 can then removed from the installation device 20, as shown in FIG. 18, allowing the installation device 20 device to be subsequently removed when the procedure is completed.

Figure 23:
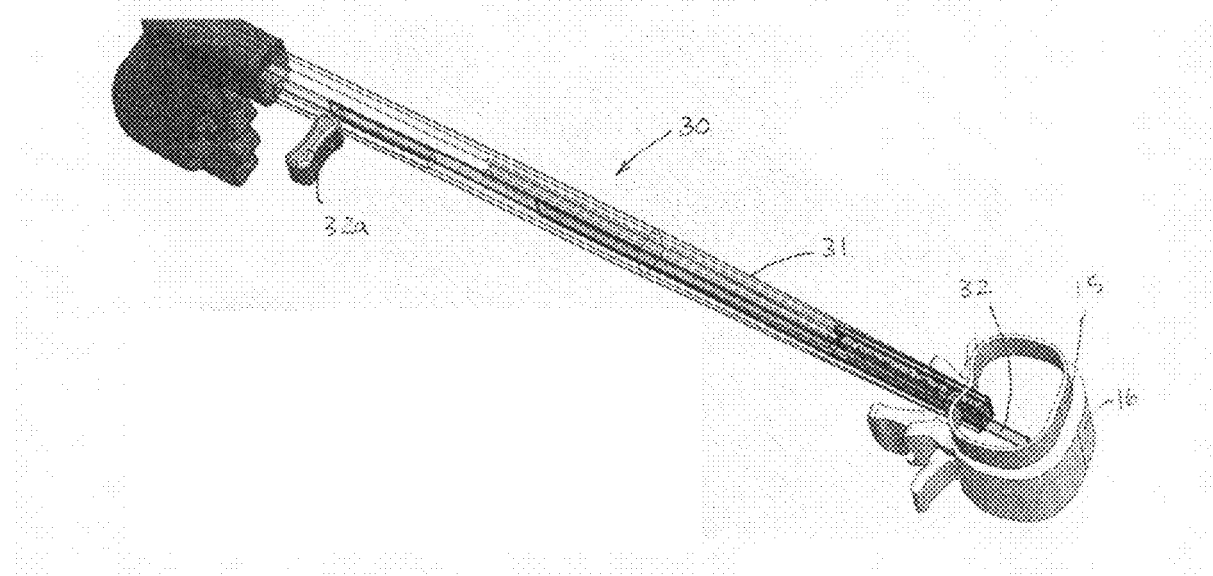
Figures 24, 25, 26, 27, 28, 29:
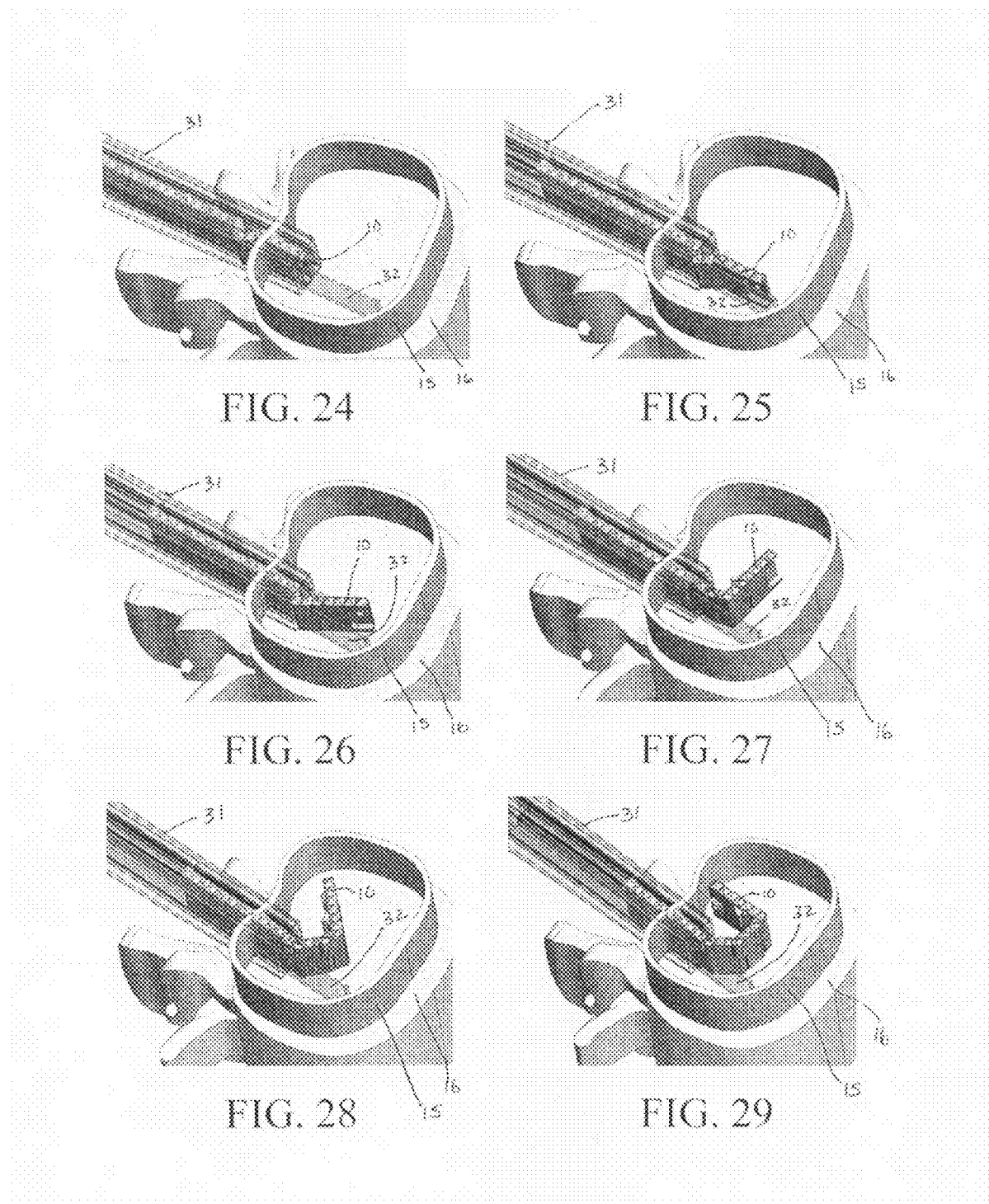
Figure 30:
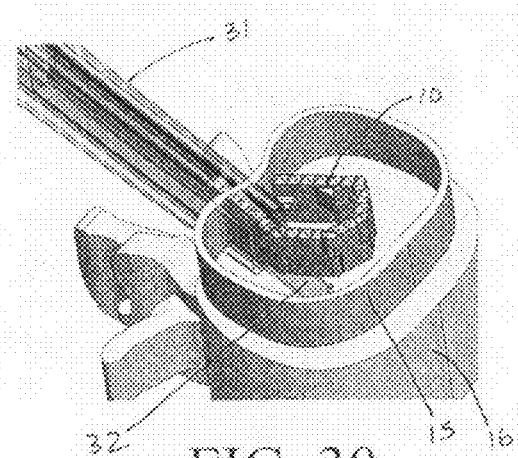
Figure 31:
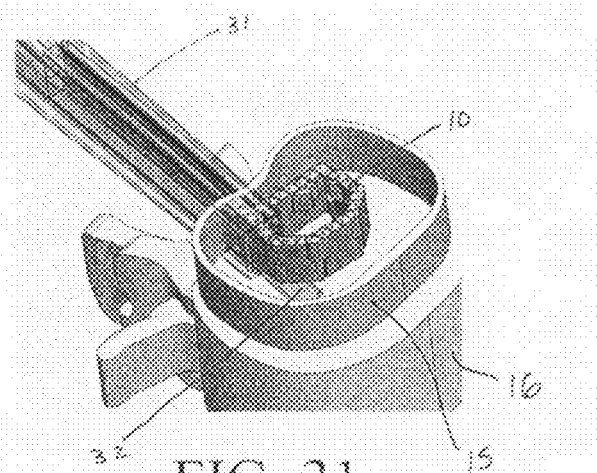
Figure 32:
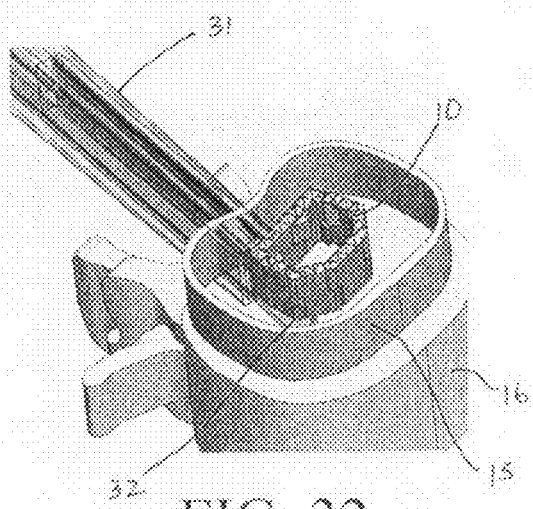
Figure 33:
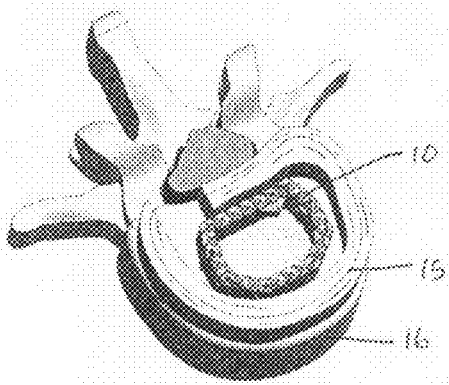
FIG. 33 is a perspective of the inter-vertebral cage illustrated in FIG. 1 in its final installed orientation within an inter-vertebral disc.

FIGS. 22 through 33 illustrate a second embodiment of an installation device, indicated generally at 30, that can be used to install the inter-vertebral cage 10 illustrated in FIG. 1 within the damaged inter-vertebral disc 15 between the adjacent vertebrae 16 and 17. The second embodiment of the installation device 30 (and its method of use) are similar in structure and operation to that of the first embodiment of the installation device 20 described above. In this second embodiment, however, the cage 10 is deployed directly from the endoscope 31 (i.e., no cartridge is provided). To facilitate this, the endoscope 31 is generally rectangular in shape. A shield 32 may be provided having a leading end that is initially deployed within the interior of the damaged inter-vertebral disc 15, as shown in FIGS. 23 and 24. A handle 32a may be provided on the second embodiment of the installation device 30 to control the movement of the shield 32 into and out of the interior of the damaged inter-vertebral disc 15. As shown in FIGS. 25 through 33, however, the installation of the cage 10 is essentially the same as described above.

Rather than relying upon internal torsional stresses that are created when the cage sections are moved into the extended orientation from the installed orientation, the hinge elements may be formed from other materials that are adapted to create the internal torsional stresses when exposed to an external condition such as, but not limited to, temperature, light, magnetic field, electric field, pressure, sound, vibration, etc. A variety of such materials are known in the art. In this instance, the hinge elements of the cage 10 would become torsionally stressed when installed within the damaged inter-vertebral disc 15. The creation of these torsional stresses may happen automatically (such as by virtue of temperature changes when the cage 10 is installed within the damaged inter-vertebral disc 15) or they may be induced by the surgeon while the cage 10 is being installed (such as by the application of another external condition).

Figure 34:
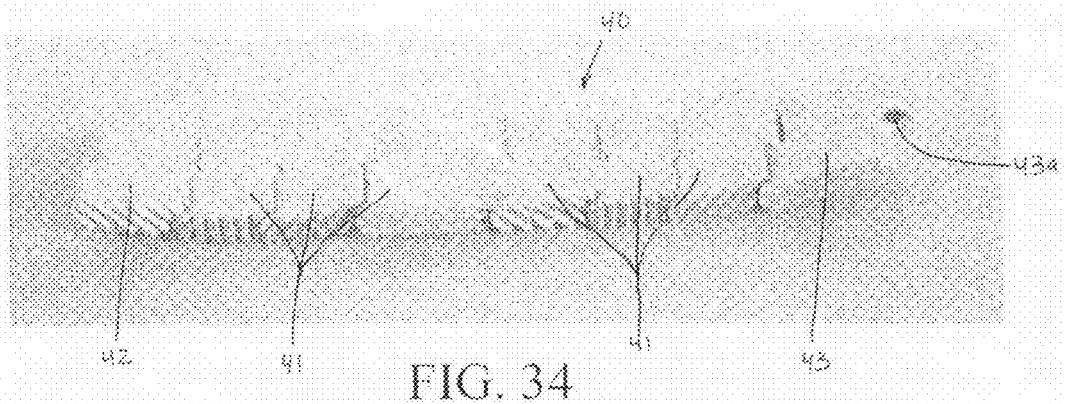
FIG. 34 is a perspective view of a second embodiment of an inter-vertebral cage in accordance with this invention shown in an initial extended orientation.
Figure 35:
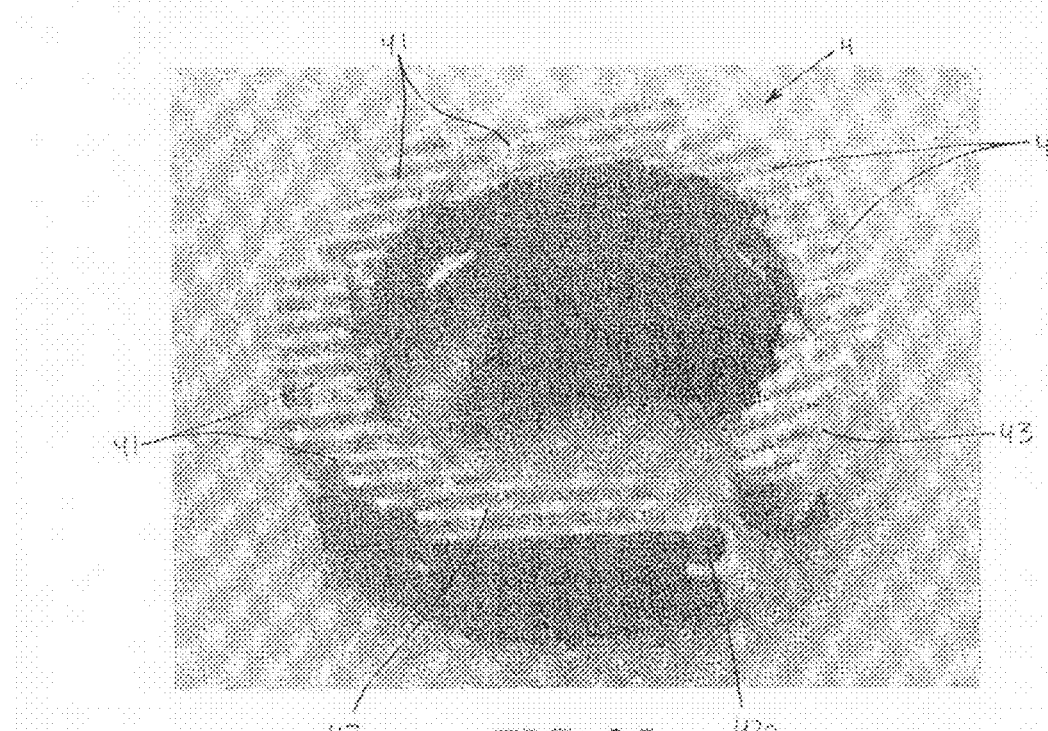
FIG. 35 is a perspective view of the second embodiment of an inter-vertebral cage illustrated in FIG. 34 shown in a final installed orientation.

FIGS. 34 and 35 illustrate a second embodiment of an inter-vertebral cage, indicated generally at 40, in accordance with this invention. FIG. 34 shows the cage 40 in an initial extended orientation, while FIG. 35 shows the cage 40 in an installed orientation. The second embodiment of the cage 40 is similar to the first embodiment 10 described above and includes a plurality of cage sections 41 and first and second end sections 42 and 43 that can be connected together in the manner described above. In this second embodiment, however, the first and second end sections 42 and 43 support respective magnets 42a and 43a. The magnets 42a and 43a can be used for both closing first and second end sections 42 and 43 of the cage 41 and for encouraging bone growth. Although any material or materials may be used for the magnets 42a and 43a, one preferred material is a neodymium magnet, also known as NdFeB, NIB, or neo magnet. The second embodiment of the cage 40 can be installed and used in the same manner as described above.

Figure 36:
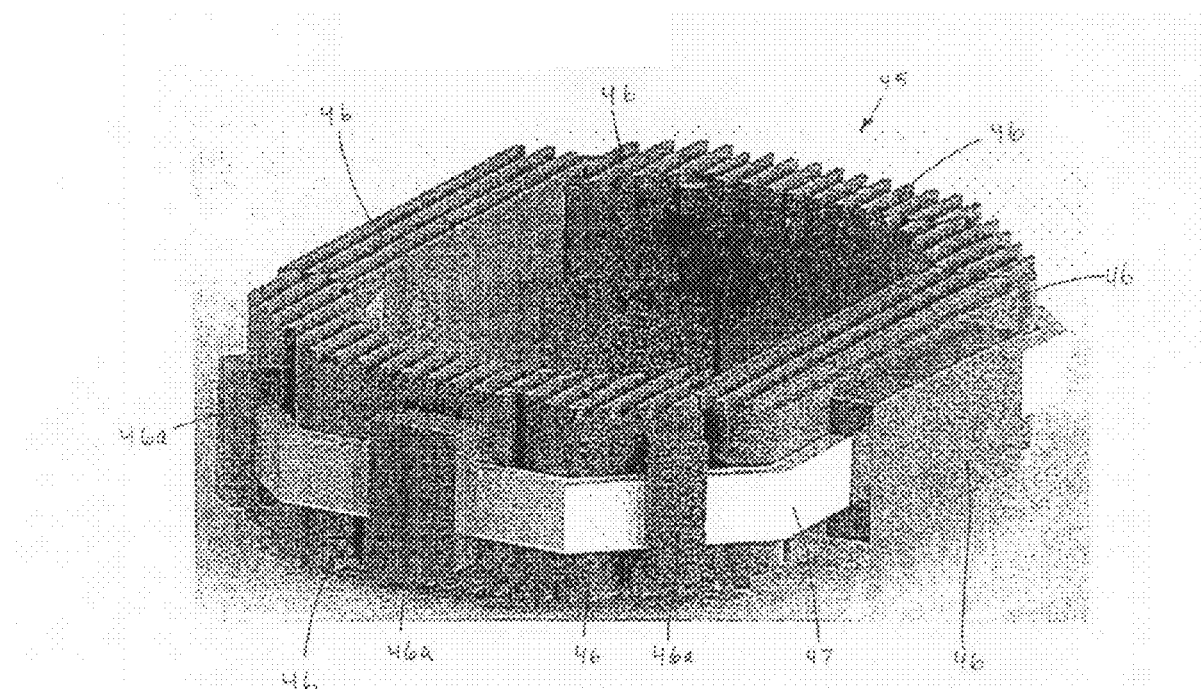
FIG. 36 is a perspective view of a third embodiment of an inter-vertebral cage in accordance with this invention shown in a final installed orientation.

FIG. 36 illustrates a third embodiment of an inter-vertebral cage, indicated generally at 45, in accordance with this invention. The third embodiment of the cage 45 is similar to the first embodiment 10 described above and includes a plurality of cage sections 46. In this third embodiment, however, some or all of the cage sections 46 are provided with loops 46a, and a belt 47 extends through such loops about the cage sections 46 to retain the cage 45 in its installed orientation shown in FIG. 36. The belt 47 can be formed from any desired material. For example, the belt 47 can be formed from a relatively flexible material that allows the cage 45 to assume the installed orientation under the urging of the hinge elements (not shown) as described above. Thereafter, the ends of the belt 47 can be secured together to retain the cage 45 in its installed orientation shown in FIG. 36.

Alternatively, the belt 47 can be formed from a material that is similar to the material used to form the hinge elements, and the torsionally stressed hinge elements 14 can be replaced by conventional hinge structures that do not automatically operate the cage 45 from the initial extended orientation to the installed orientation. In this instance, the belt 47 functions to automatically urge the cage 45 to assume the installed orientation as the cage 45 is extended into the interior of the damaged inter-vertebral disc 15. As a result, no additional fastener would necessarily be needed to retain the cage 45 in its installed orientation shown in FIG. 36.

Figure 37:
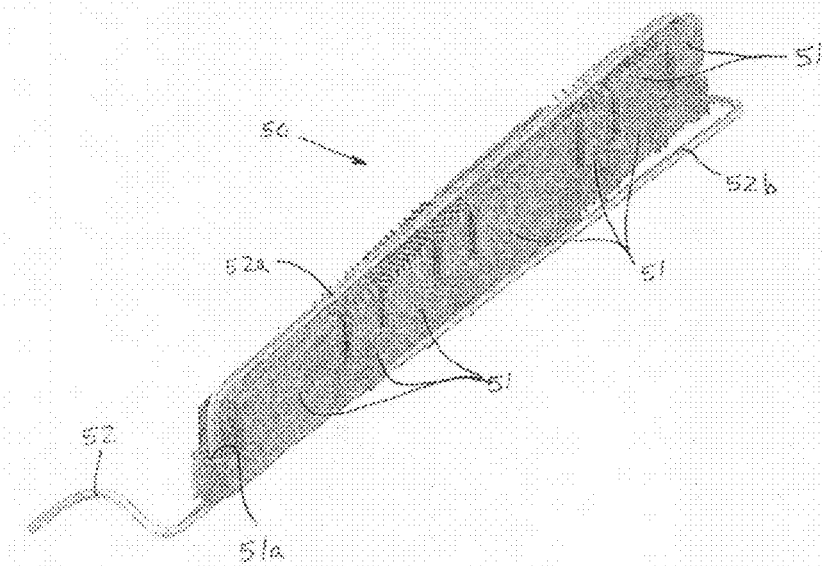
FIG. 37 is a perspective view of a fourth embodiment of an inter-vertebral cage in accordance with this invention shown in an initial extended orientation.

FIG. 37 illustrates a fourth embodiment of an inter-vertebral cage, indicated generally at 50, in accordance with this invention. The fourth embodiment of the cage 50 is similar to the first embodiment 10 described above and includes a plurality of cage sections 51. In this fourth embodiment, however, the torsionally stressed hinge elements 14 can be replaced by conventional hinge structures that do not automatically operate the cage 50 from the initial extended orientation to the installed orientation. Rather, a wire 52 is used to actuate the cage 50 from its initial extended orientation illustrated in FIG. 35 to the closed final assembly orientation described above. In the illustrated embodiment, the wire 52 includes a first portion 52a that extends generally along an upper surface of the cage 50 and a second portion 52b that extends generally along a lower surface thereof. The end of the second portion 52b of the wire 52 can be secured to one of the cage section 51 or to the first portion 52a of the wire 52 in the manner of a slip knot. At least one of the first and second portions 52a and 52b of the wire 52 (the lower portion 52b in FIG. 35) is laterally offset from the cage 50. The wire 50 may pass through apertures 51a provided in one or more of the cage sections 51.

The cage 50, its initial extended orientation, can be installed within the interior of the damaged inter-vertebral disc 15 in the manners described above. As such installation is occurring, the wire 52 is pulled or otherwise placed in tension. Because of the lateral offset of the second portion 52b of the wire 52, such tension causes the cage sections 51 to move relative to one another until the cage 50 is moved from the initial extended orientation to the installed orientation. The wire 52 can also be used to secure the ends of the cage 50 together, thereby eliminating the need for a separate fastener. Alternatively, the wire 52 can be formed from a material that is similar to the material used to form the hinge elements. In this instance, the wire 52 functions to automatically urge the cage 50 to assume the installed orientation as the cage 50 is extended into the interior of the damaged inter-vertebral disc 15. Again, no additional fastener would necessarily be needed to retain the cage 50 in its installed orientation. Alternatively, however, the wire 52 can be locked using a lockable washer (not shown) or by crimping.

Figure 38:
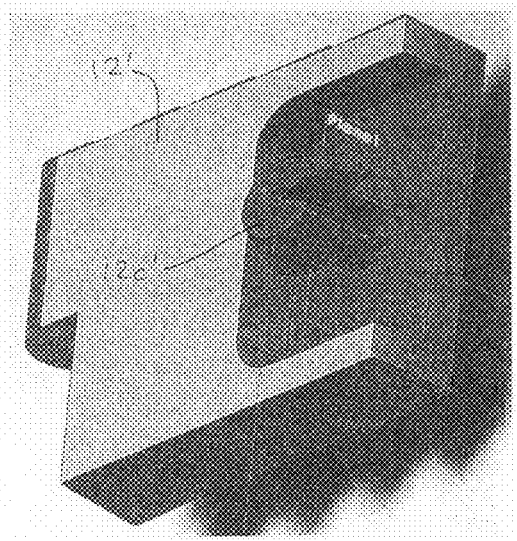
FIG. 38 is an enlarged perspective view of a male end section that can be used in conjunction with any of the above embodiments of the inter-vertebral cage.
Figure 39:
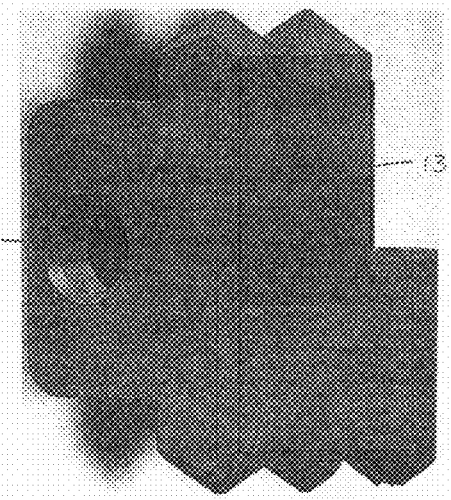
FIG. 39 is an enlarged perspective view of a female end section that can be used in conjunction with any of the above embodiments of the inter-vertebral cage.
Figure 40:
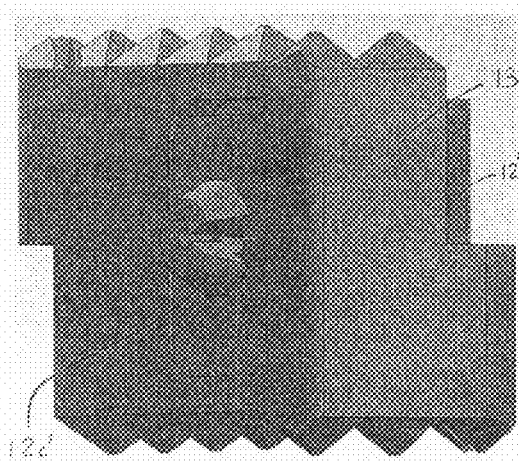
FIG. 40 is an enlarged perspective view of the male and female end sections illustrated in FIGS. 38 and 39 shown assembled.
Figure 41:
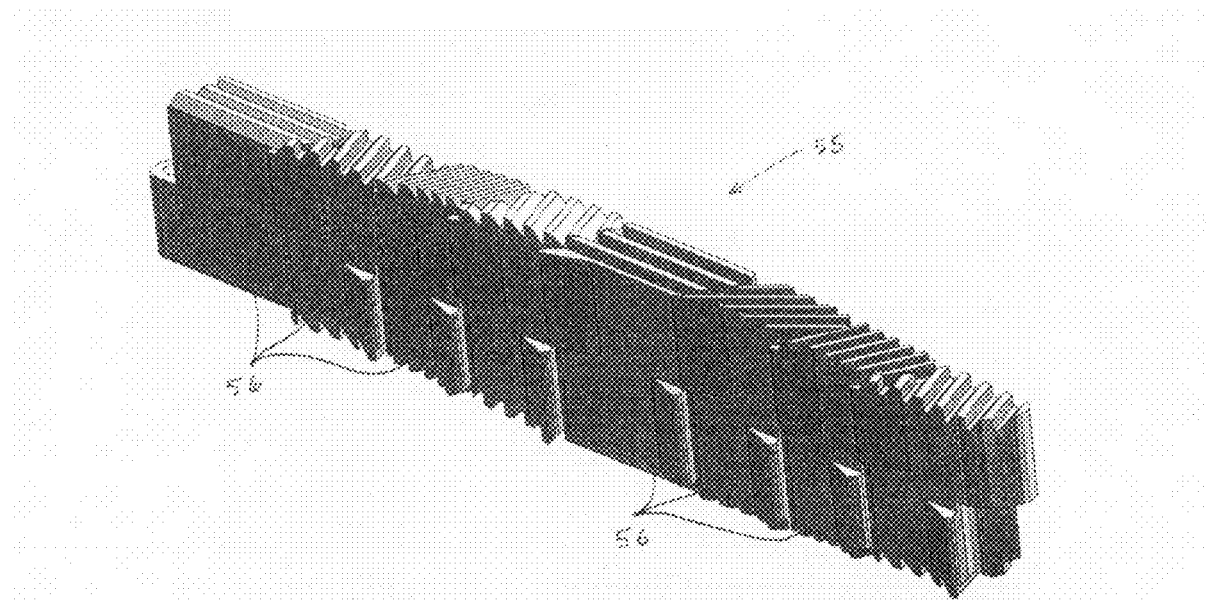
FIG. 41 is a perspective view of a fifth embodiment of an inter-vertebral cage in accordance with this invention shown in an initial extended orientation.

FIGS. 38 through 40 illustrate alternative locking structures 12c' and 13b' that can be provided on modified versions of the first and second end sections 12' and 13' to positively retain them together when the cage 10 is in its final installed orientation. As shown in FIG. 38, the modified first end section 12' has a protrusion 12c' provided thereon. In the illustrated embodiment, the protrusion 12c' is a bayonet-type of fastener that is formed integrally with the modified first end section 12'. However, the protrusion 12c' may be formed having any other desired shape and may be formed separately from the modified first end section 12' if desired. As shown in FIG. 39, the modified second end section 13' has an opening 13b' formed therethrough that is sized and positioned to cooperate with the protrusion 12c'. Thus, when it is desired to positively retain the first and second end sections 12' and 13' together when the cage 10 is in its final installed orientation, the protrusion 12c' is inserted through the opening 13b' in a snap fit manner. The protrusion 12c' and the opening 13b' may be sized and shaped to allow the first and second end sections 12' and 13' to be subsequently disconnected if desired.

Figure 42:
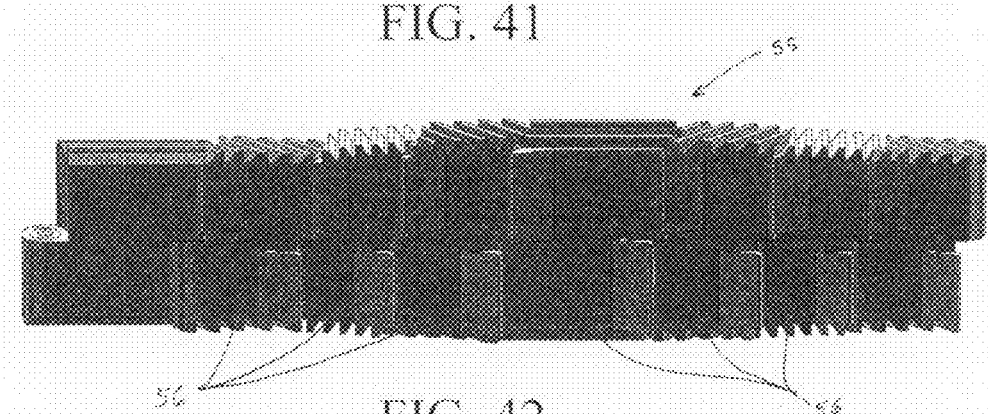
FIG. 42 is a side elevational view of the fifth embodiment of the inter-vertebral cage illustrated in FIG. 41.
Figure 43:
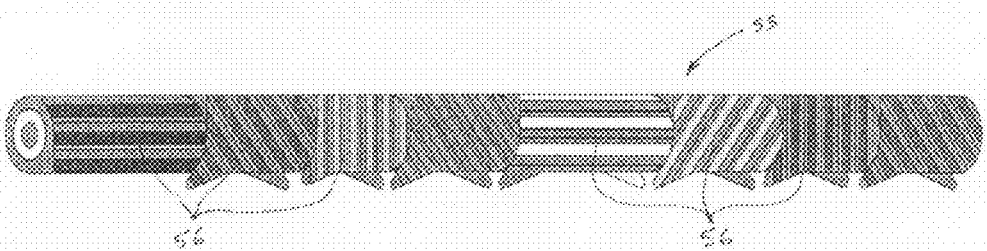
FIG. 43 is a top plan view of the fifth embodiment of the inter-vertebral cage illustrated in FIGS. 41 through 42.
Figure 44:
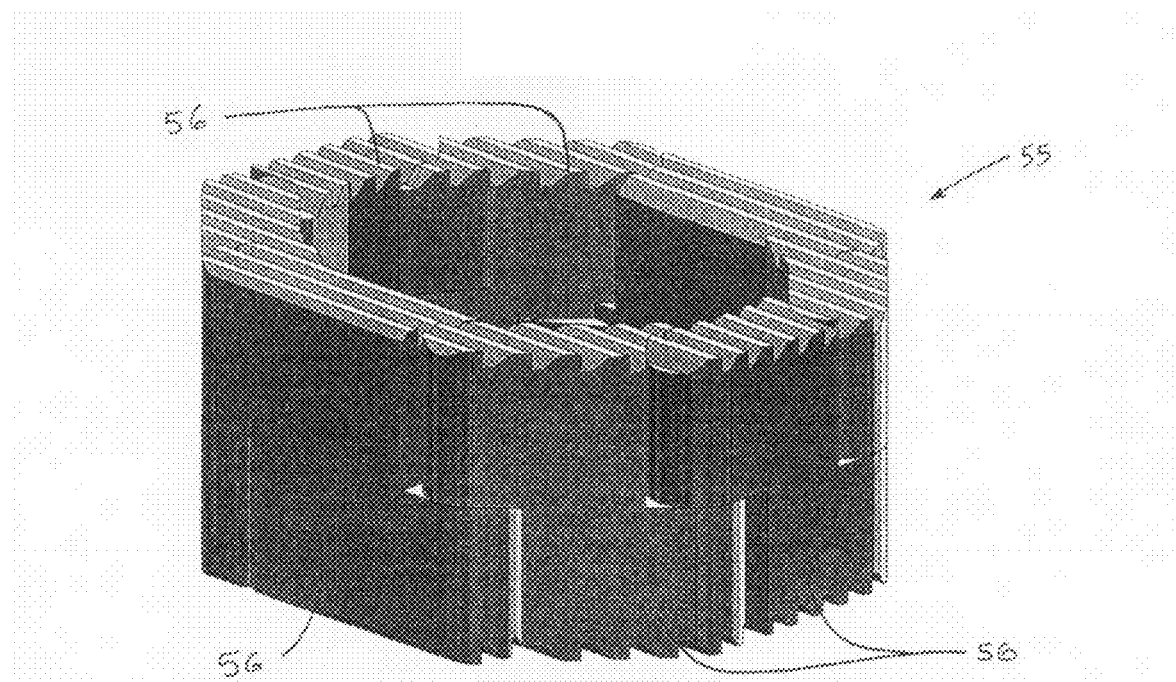
FIG. 44 is a perspective view of the fifth embodiment of the inter-vertebral cage illustrated in FIGS. 41 through 43 shown in a final installed orientation.
Figure 45:
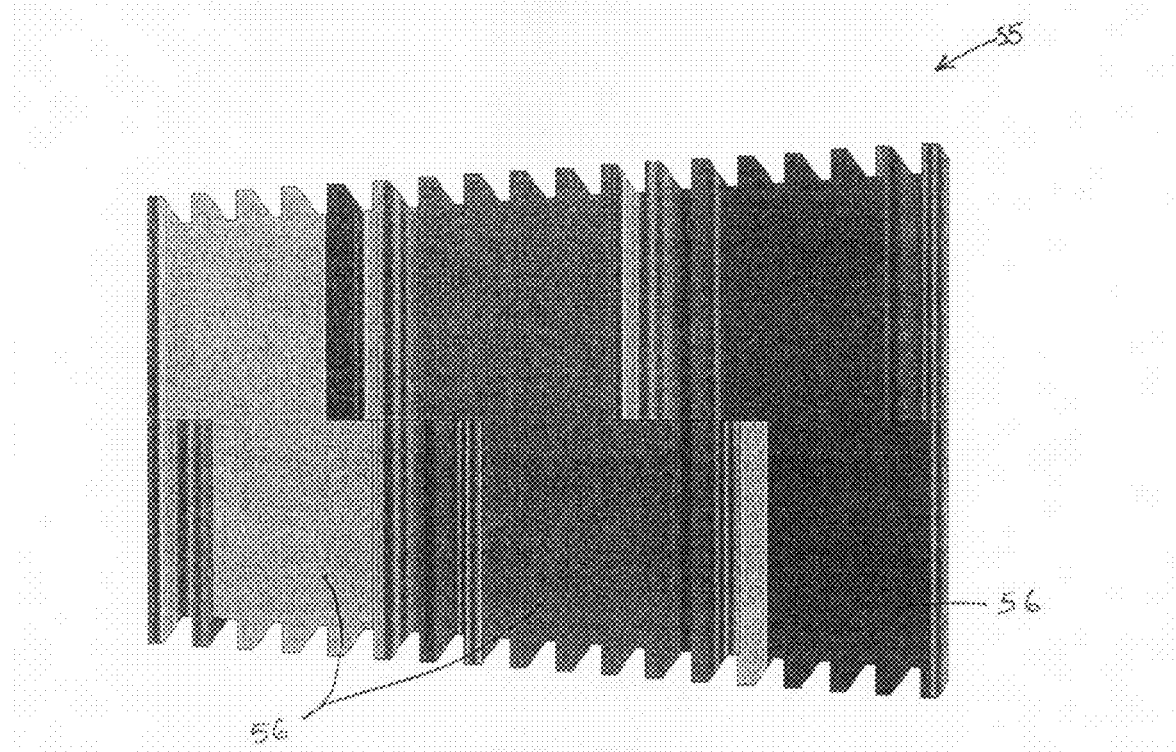
FIG. 45 is an enlarged end elevational view of the fifth embodiment of the inter-vertebral cage illustrated in FIGS. 41 through 44.

FIGS. 41 through 45 illustrate a fifth embodiment of an inter-vertebral cage, indicated generally at 55, in accordance with this invention. The fifth embodiment of the cage 55 is similar to the first embodiment 10 described above and includes a plurality of cage sections 56 that are connected together by hinge elements (not shown). In this fifth embodiment, however, some or all of the cage sections 56 are formed having different sizes. For example, as best shown in FIG. 42, the cage sections 56 provided in the center portion of the cage 55 are longer in the direction between the upper and lower surfaces thereof than the cage sections 56 provided in the end portions of the cage 55. Thus, when the cage is in its installed orientation illustrated in FIG. 45, one side of the cage 55 (the left side when viewing FIG. 45) is taller or otherwise greater in dimension than the opposite side (the right side when viewing FIG. 45). This type of cage 55 can be useful in treating lordosis or other curvatures of the spine.

As described above, the cage 10 can be implanted using an endoscopic 20. However, it will be appreciated that the cage 10 can be implanted without the use of the endoscope 20. In such an instance, it is still preferred that the cage 10 be implanted using a minimally invasive surgical technique, the use of which is facilitated by the automatic deployment of the cage 10 as described above. However, the cage 10 can be implanted in any desired manner.

Because the posterior lumbar interbody fusion is one of the most flexible procedures (being able to access all lumbar and sacral motion segments) but also one of the most dangerous due to its close proximity to the spinal cord, it was deemed that a minimally invasive device would be most suited for application in this surgical approach. The cage presented herein requires a much smaller incision compared to existing cages due to the fact that, prior to insertion, this device can be elongated such that an incision as small as the width of only one wall segment is necessary for placement as seen in FIG. 1. The entirety of the device and graft material can be properly placed within the inter-vertebral body through this one incision. This smaller surgical footprint minimizes many of the complications associated with this approach. Since the current cage design is only 6 mm at its widest point and it only requires a solitary incision, the device will reduce the need for mobilization of the dural sac thus minimizing the risks of spinal fluid leak and durotomy. Also, this smaller, single incision will eliminate the need to remove all or most of the posterior support structures and will therefore increase overall structural stability and reduce the risk of transitional syndrome. Furthermore, decreased disruption of the annulus fibrosus will increase structural stability of the fusion construct as well as provide higher, consistent, compressive loads necessary for a more successful fusion. This results from the fact that tension within the annulus can be maintained around the entire circumference as opposed to other fusion procedures that involve the elimination of large sections of the annulus and therefore can create instability in those regions.

The machined geometries and features of the cage segments themselves also serve an important role in the overall performance of the cage. Pyramid-shaped geometries machined into the top of each wall segment are designed to puncture into the adjacent vertebral body to provide anchorage and thus minimize cage movement in any direction and therefore reduce dependence on hinge forces to maintain a rigid structure. The "z shape" of the nitinol hinge wires was developed to transmit the rotational motion of segments into torque within the wire more readily. An illustration of the "z-shaped" design and schematic of rotation transmitted through the wire can be seen in FIG. 4. Grooves cut into each of the segments, highlighted with a blue circle in FIG. 5, are meant to guard the "z-shaped" hinge wire and transmit the loads from the wire directly to the cage walls. Since the wire is designed to fit snugly within this feature, the forces produced through rotation of the wall segments can be transmitted directly to the edges of the feature rather than through a tack weld that is used to hold the wires in place. This will reduce the loads applied to the weld (if any) and therefore reduce the risk of failure at this critical junction. Internal junction walls, highlighted in green and yellow in FIG. 6, are meant to act as stopping blocks for segments. These features will limit the motion of the hinge wires while the cage is being implanted and will then act as structural braces once the device is locked in the enclosed orientation taking dependence off of the hinge wires themselves. Finally, the open design of the device itself allows for the surgeon to move and adjust it to allow for proper placement and insertion of various types of bone graft material. Since surgeons may prefer, or patients may require, one graft material over another, it is best to not limit the choices a surgeon has in the implementation of a particular device.

All of the various components and features described herein are meant to create a cage that will require shorter procedural time, minimize the risk of complications, and consequently, result in a shorter recovery time for the patient.

The principle and mode of operation of this invention have been explained and illustrated in its preferred embodiments. However, it must be understood that this invention may be practiced otherwise than as specifically explained and illustrated without departing from its spirit or scope.

What is claimed is:

1. An inter-vertebral cage comprising:
a plurality of cage sections each having an upper surface and a lower surface, a first recess extending externally along the upper surface from a first aperture formed through the cage section, and a second recess extending externally along the lower surface from a second aperture formed through the cage section;
hinge elements that connect adjacent ones of the cage sections together for relative movement by extending through aligned apertures of adjacent ones of the cage sections, the hinge elements urging the cage sections to move from an extended orientation to an installed orientation, the hinge elements each comprising a central body and a first end and a second end extending from the central body at angles, wherein the central body extends through the aligned apertures of adjacent ones of the cage sections, the first end being received in the first recess along the upper surface of a first one of the cage sections, and the second end being received in the second recess along the lower surface of a second one of the cage sections; and
first and second end sections that are connected to the plurality of cage sections, wherein the first and second end sections have respective locking structures provided thereon for selectively retaining the first and second end sections together.

2. The inter-vertebral cage defined in claim 1 wherein the hinge elements urge adjacent ones of the cage sections to extend at an angle relative to one another.

3. The inter-vertebral cage defined in claim 1 wherein each of the hinge elements have greater torsional stresses when the cage sections are in the extended orientation than when the cage sections are in the installed orientation.

4. The inter-vertebral cage defined in Claim 1 wherein the first and second ends of the hinge elements are received in respective internal recesses provided within the cage elements.

5. The inter-vertebral cage defined in claim 1 wherein the hinge elements are formed from a shape memory alloy material.

6. The inter-vertebral cage defined in claim 1 wherein the locking structures include a recess provided on the first end section and a tab provided on the second end section that cooperates with the recess.

7. The inter-vertebral cage defined in claim 1 wherein the locking structures include openings provided on the first and second end sections and a fastener that extends through the openings.

8. The inter-vertebral cage defined in claim 1 wherein the locking structures include a protrusion provided on the first end section and an opening provided on the second end section that cooperates with the protrusion.

9. The inter-vertebral cage defined in claim 1 wherein the locking structures include magnets provided on the first and second end sections.

10. The inter-vertebral cage defined in claim 1 wherein a belt extends about the cage for selectively retaining the cage in the installed orientation.

11. The inter-vertebral cage defined in claim 1 wherein a wire having an offset portion selectively retains the cage in the installed orientation.

12. The inter-vertebral cage defined in claim 1 wherein the hinge elements are formed from a material that is adapted to create the internal torsional stresses when exposed to an external condition.

13. The inter-vertebral cage defined in claim 12 wherein the external condition is one of temperature, light, magnetic field, electric field, pressure, sound, and vibration.

14. The inter-vertebral cage defined in claim 1 wherein some or all of the cage sections are formed having different sizes.

15. The inter-vertebral cage defined in claim 14 wherein the cage sections provided in a center portion of the cage are longer than the cage sections provided in end portions of the cage.

16. A device for installing an inter-vertebral cage within an inter-vertebral disc comprising:
an endoscope having an opening provided therein; and
an inter-vertebral cage disposed within the opening, the inter-vertebral cage including a plurality of cage sections each having an upper surface and a lower surface, a first recess extending externally along the upper surface from a first aperture formed through the cage section, a second recess extending externally along the lower surface from a second aperture formed through the cage section, and hinge elements that connect adjacent ones of the cage sections together for relative movement by extending through aligned apertures of adjacent ones of the cage sections, the hinge elements urging the cage sections to move from an extended orientation to an installed orientation, the hinge elements each comprising a central body and a first end and a second end extending from the central body at angles, wherein the central body extends through the aligned apertures of adjacent ones of the cage sections, the first end being received in the first recess along the upper surface of a first one of the cage sections, and the second end being received in the second recess along the lower surface of a second one of the cage sections.

17. The installation device defined in claim 16 further including a cartridge that is disposed within the opening, and wherein the inter-vertebral cage is disposed within the cartridge.

18. The installation device defined in claim 17 wherein the cartridge is movable relative to the endoscope.

19. The installation device defined in claim 18 wherein the cartridge has a locator ridge provided thereon that cooperates with a locator recess provided on the endoscope such that the cartridge may be inserted within the endoscope in a single, predetermined orientation relative thereto.

20. The installation device defined in claim 18 wherein the cartridge has a plurality of teeth formed on an outer surface thereof to facilitate movement of the cartridge relative to the endoscope.

21. The installation device defined in claim 18 wherein the cartridge has a stop flange provided thereon that limits the amount by which the cartridge may be moved relative to the endoscope.

22. The installation device defined in claim 16 wherein the endoscope further includes a second opening having a camera provided therein.

23. The installation device defined in claim 22 wherein the endoscope further includes a third opening having a cannula provided therein.

24. A method of repairing a damaged inter-vertebral disc comprising the steps of:
(a) removing a portion of an annulus fibrosus and the nucleus of a damaged intervertebral disc to provide a space therein; and
(b) installing an inter-vertebral cage within the space of the damaged intervertebral disc, wherein the inter-vertebral cage includes a plurality of cage sections each having an upper surface and a lower surface, a first recess extending externally along the upper surface from a first aperture formed through the cage section, a second recess extending externally along the lower surface from a second aperture formed through the cage section, and hinge elements that connect adjacent ones of the cage sections together for relative movement by extending through aligned apertures of adjacent ones of the cage sections, the hinge elements urging the cage sections to move from an extended orientation to an installed orientation, the hinge elements each comprising a central body and a first end and a second end extending from the central body at angles, wherein the central body extends through the aligned apertures of adjacent ones of the cage sections, the first end being received in the first recess along the upper surface of a first one of the cage sections, and the second end being received in the second recess along the lower surface of a second one of the cage sections.

25. The method defined in claim 24 wherein step (b) is performed by providing an endoscope having an opening provided therein, initially disposing the intervertebral cage within the opening in the extended orientation, and subsequently moving the inter-vertebral cage through the opening into the damaged inter-vertebral disc to automatically assume the installed orientation.

26. The method defined in claim 25 wherein the endoscope includes a camera that allows direct viewing of steps (a) and (b) as they are being performed.

* * * * *